(12) United States Patent
Harnack et al.

(10) Patent No.: US 8,842,274 B2
(45) Date of Patent: Sep. 23, 2014

(54) CUVETTE WITH INSERT AND ADAPTER

(75) Inventors: Kurt Harnack, Tangstedt (DE); Helmut Knoffe, Norderstedt (DE); Peter Scheffler, Hamburg (DE); Wolfgang Goemann-Thoss, Hamburg (DE); Sven Eikelmann, Hamburg (DE); Christoph Jolie, Hamburg (DE)

(73) Assignee: Eppendorf AG, Hamburg (DE)

( * ) Notice: Subject to any disclaimer, the term of this patent is extended or adjusted under 35 U.S.C. 154(b) by 905 days.

(21) Appl. No.: 12/933,789

(22) PCT Filed: Mar. 23, 2009

(86) PCT No.: PCT/EP2009/002121
§ 371 (c)(1),
(2), (4) Date: Mar. 21, 2011

(87) PCT Pub. No.: WO2009/115345
PCT Pub. Date: Sep. 24, 2009

(65) Prior Publication Data
US 2011/0170094 A1   Jul. 14, 2011

Related U.S. Application Data

(60) Provisional application No. 61/038,596, filed on Mar. 21, 2008.

(51) Int. Cl.
| | |
|---|---|
| *G01N 1/10* | (2006.01) |
| *B01L 3/00* | (2006.01) |
| *G01N 21/03* | (2006.01) |
| *B01L 9/00* | (2006.01) |
| *B01L 3/18* | (2006.01) |

(52) U.S. Cl.
CPC ......... *G01N 21/03* (2013.01); *B01L 2300/0809* (2013.01); *B01L 3/5088* (2013.01); *B01L 3/18* (2013.01); *B01L 2300/043* (2013.01); *G01N 2021/0307* (2013.01); *G01N 2021/035* (2013.01); *B01L 9/52* (2013.01); *B01L 2200/021* (2013.01)
USPC ....................................................... 356/246

(58) Field of Classification Search
USPC ........... 356/244, 246; 250/576; 422/102, 104, 422/547, 561–562, 65, 82.09
See application file for complete search history.

(56) References Cited

U.S. PATENT DOCUMENTS

| | | | |
|---|---|---|---|
| 4,332,471 A | 6/1982 | Gross | |
| 4,682,890 A | 7/1987 | de Macario et al. | |

(Continued)

FOREIGN PATENT DOCUMENTS

| | | | |
|---|---|---|---|
| DE | 27 26 498 A1 | 12/1978 | |
| DE | 19826470 A1 | 12/1999 | |

(Continued)

*Primary Examiner* — Tarifur Chowdhury
*Assistant Examiner* — Michael P Lapage
(74) *Attorney, Agent, or Firm* — Vidas, Arrett & Steinkraus, P.A.

(57) ABSTRACT

Cuvette, comprising at least one measuring area on each one of two arms that are pivotally connected to each other such that from a swung-apart condition, they can be swung together into a measuring position in which the two measuring areas have a distance for positioning a sample between the measuring areas, and means for positioning the two arms in a measuring position in a cuvette shaft of an optical measuring device with a sample between the two measuring areas in a beam path of the optical measuring device that crosses the cuvette shaft.

30 Claims, 17 Drawing Sheets

(56) References Cited

U.S. PATENT DOCUMENTS

| | | | |
|---|---|---|---|
| 5,208,649 A * | 5/1993 | Cuppoletti et al. | 356/244 |
| 5,289,255 A * | 2/1994 | Mullin et al. | 356/246 |
| 5,306,467 A * | 4/1994 | Douglas-Hamilton et al. | 422/551 |
| 5,331,398 A | 7/1994 | Eggl et al. | |
| 5,601,991 A | 2/1997 | Oberhardt | |
| 5,795,748 A | 8/1998 | Cottingham | |
| 6,249,345 B1 * | 6/2001 | Kraack et al. | 356/246 |
| 2002/0116897 A1 | 8/2002 | Higashizaki et al. | |
| 2002/0140931 A1 | 10/2002 | Robertson | |
| 2005/0270642 A1 * | 12/2005 | McLellan et al. | 359/391 |
| 2006/0077390 A1 | 4/2006 | Kralik | |
| 2007/0019189 A1 | 1/2007 | Marsteller et al. | |
| 2009/0290153 A1 * | 11/2009 | Juhl | 356/319 |
| 2011/0149280 A1 * | 6/2011 | Juhl | 356/319 |

FOREIGN PATENT DOCUMENTS

| | | | |
|---|---|---|---|
| JP | 356147069 A * | 11/1981 | G01N 35/02 |
| JP | 2007271560 A | 10/2007 | |
| WO | 9936764 | 7/1999 | |
| WO | 0075632 A1 | 12/2000 | |
| WO | 2005114146 A1 | 12/2005 | |
| WO | 2006086459 A2 | 8/2006 | |
| WO | 2007111555 A1 | 10/2007 | |
| WO | 2007111838 A2 | 10/2007 | |

* cited by examiner

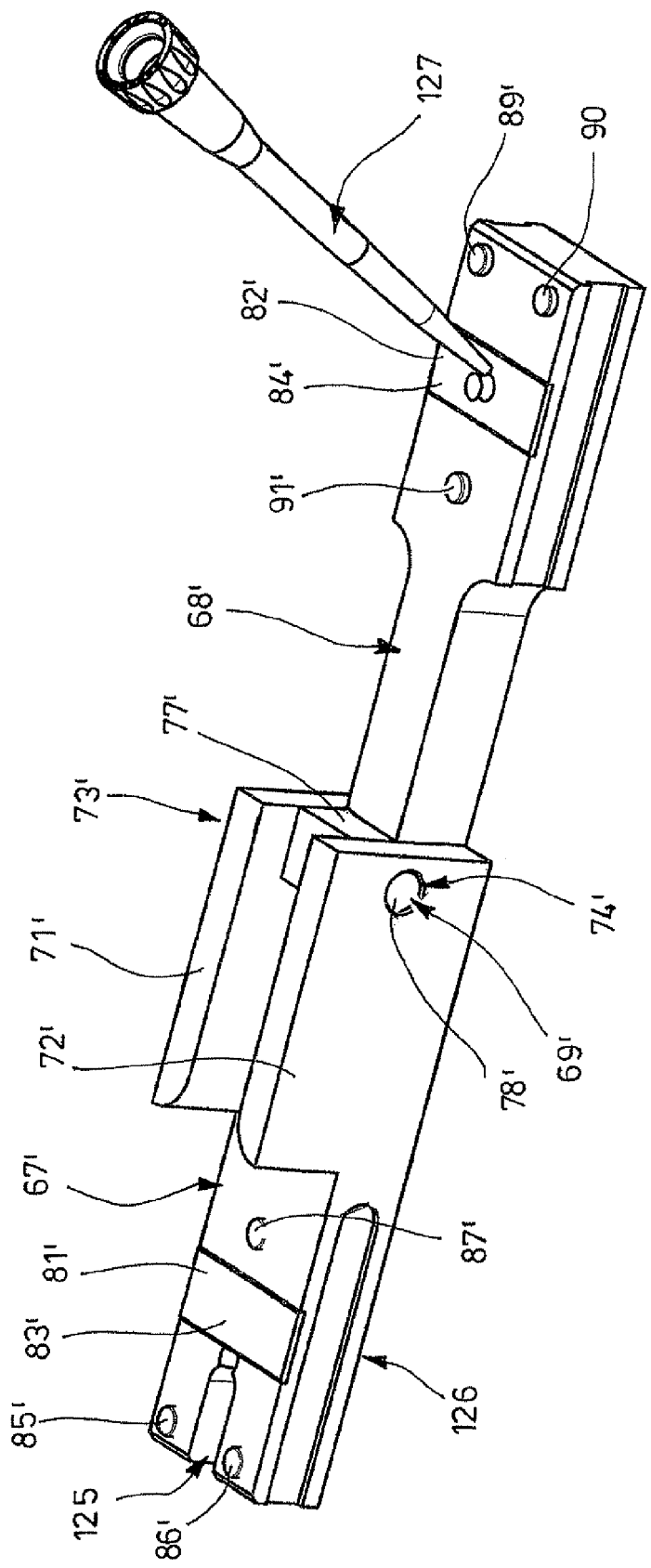
FIG.13.1

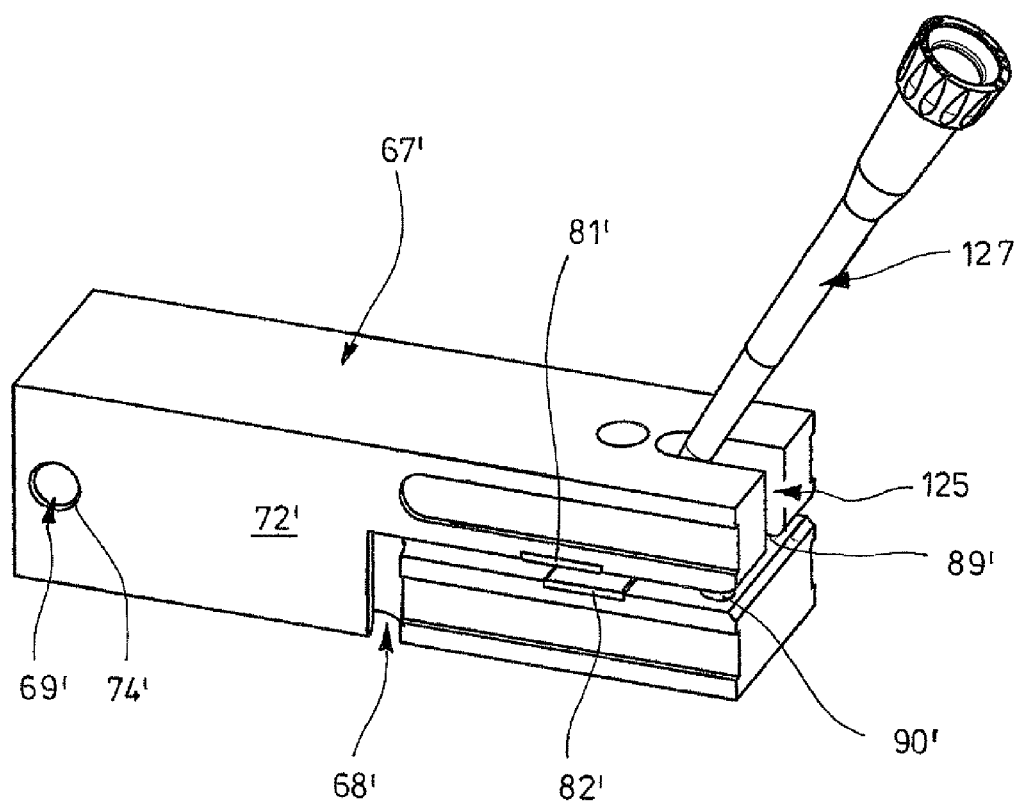
FIG.14.1

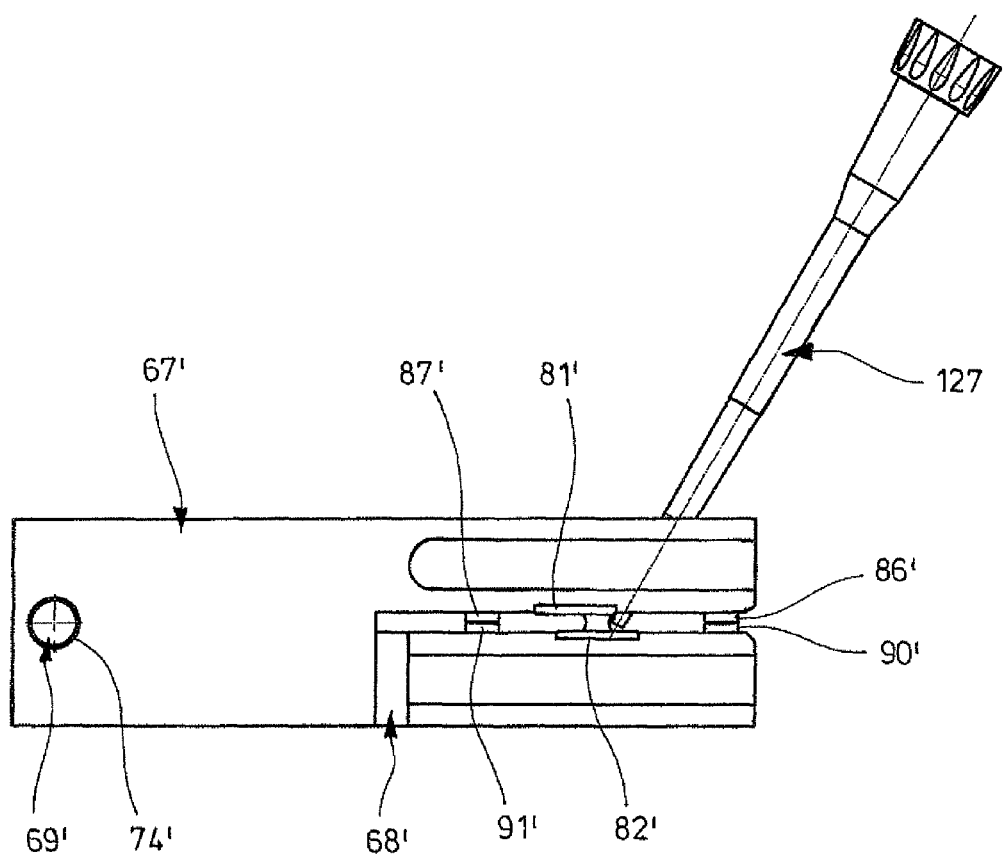
FIG.14.2

CUVETTE WITH INSERT AND ADAPTER

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to the analysis of liquid samples with a spectrometer or photometer or other optical measuring devices. Such analyses are made typically, but not exclusively, in the molecular-biological, biochemical, inorganic-chemical, and organic-chemical and foodstuff chemical laboratory. Samples are optically analysed for instance in research, in diagnostics and in quality control. They are analysed for instance by way of absorption-, reflection-, emission-, fluorescence-, Raman- or luminescence spectroscopy in the UV-VIS or IR wavelength range. Examples for analytes to be measured are biomolecules like nucleic acids, proteins, lipids as well as inorganic or organic materials and compounds. These analytes can be measured directly or after a chemical reaction that serves for facilitating the spectrometric or photometric analysis.

The present invention is related in particular to all the applications that were mentioned by way of example above. An essential field of its application is the measurement of valuable samples in small amounts in molecular biology. Often only small amounts of sample are at hand (for instance, from less than 1 up to 5 micro-liters), because nor more material can be obtained. When diluting the samples, the measurement results would become too inaccurate due to decreased absorption. A typical application is the photometric or fluorometric measurement of nucleic acid concentrations before a PCR or real-time PCR, in order to be able to use that starting amount of the nucleic acid which is optimum for PCR. Another example is the measurement of the concentration of nucleic acids and marker substances incorporated into the nucleic acid, as well as of the marking density of marked nucleic acids derived from this, in order to be able to use the optimum amount of marked nucleic acid before beginning a micro array experiment, and to be sure that the marking density of the nucleic acid is in the optimum range.

For spectrometric or photometric analysis, liquid samples are filled into cuvettes. Standard cuvettes are suited for the insertion into the cuvette shafts of most of the current spectrometers and photometers. These cuvette shafts are also called "standard cuvette shafts" in the following. Standard cuvette shafts of usual commercial optical measuring instruments having a cross section of 12.5 mm×12.5 mm have become wide-spread. The heights of the light beam above the bottom of the cuvette shaft vary from 8.5 mm to 20 mm, depending on the type of the device. Standard cuvettes have a box-like outline, wherein the cross section and the height are matched to the dimensions of the standard cuvette shafts.

Re-usable standard cuvettes of quartz glass for small amounts of sample are marketed by the companies Hellma and Starna in particular. These ultra micro cuvettes have a layer thickness of 1 mm or more. It is very difficult to fill them without bubbles, and very sumptuous to empty and to clean them. Because the main application of the optical measurements is the measurement of very small volumes when measuring nucleic acids in the UV region, they are made of quartz glass and are particularly expensive. They must be treated with much care, because they are very expensive to buy. For the ultra micro cuvettes of quartz glass that are obtainable on the market, a minimum volume of 5 micro-liters must be used, which is too much for many applications.

Other cuvettes are marketed with the designation "Mikroliter-Messzelle" (micro-liter measuring cell). Under the product name "Tray Cell®", the company Hellma, and under the product name "Label Guard" the company Implen markets a micro-liter measuring cell which corresponds to a standard cuvette in its dimensions, and may therefore be used in many of the today's spectrometers. The micro-liter measuring cell of the company Hellma is described in WO 2005/114146 A1. In order to make an analysis, one drop of about 1 to 2 micro-liters of the liquid to be analysed must be applied to the topside of a measuring window at a layer thickness of 0.2 mm, or at a layer thickness of 1 mm when the drop is 3 to 5 micro-liters. The measuring chamber is closed by a lid. The light beam of the measuring optics is guided from the radiation source through the sample to the sensor via beam deflections and fibre-optic light guides and via a mirror in the lid.

The micro-liter measuring cell is very sumptuous in its construction and it has a high price, and therefore it cannot always be used in an economically reasonable fashion. Moreover, it has a high apparatus-dependent intrinsic absorption of 1.3 E at 230 to 650 nm, about which the measurement range of the measuring instrument is reduced. Further, it is not possible to visually check the measuring solution in the measurement chamber after filling in the sample and putting up the lid, in order to detect disturbing bubbles, particles and erroneous pipettings that might lead to erroneous measurements. In addition it is disadvantageous that the user must clean the measuring window after use in a time-consuming way.

Under the product name "Nano Quant Plate", the company Tecan offers a kind of collapsible micro-plate for a microplate reader.

Under the product name "NanoDrop®", the company NanoDrop Technologies markets a photometer, which permits to analyse samples that have a volume of one micro-liter only. This spectrometer is described in WO 2006/086459 A2. The system envisions the direct optical measurement in a drop of liquid which is located between two horizontally aligned, planar surfaces. A light source illuminates the sample of liquid from the side through the gap between the two surfaces. A fibre light guide runs out into the lower surface, which leads the light further to a fibre optics spectrophotometer after it has passed through the liquid sample. Thus, the sample liquid is in direct contact with the glass fibre.

In the spectrophotometer, it is disadvantageous that the optical surface can be negatively affected by certain samples. According to the operation manual of the spectrophotometer of the type NanoDrop-1000, such samples are for instance protein containing solutions. In this case, the user must manually condition anew the optical surface after repeated usage by intense, time-consuming strong rubbing. Also, strongly acidic or alkaline solutions cannot be used.

Further, the sample is in direct, open contact with the solution. Thus, dangerous substances cannot be examined with this system. However, dangerous materials, like possibly infective substances, are often used in the molecular-biological, cell-biological, biochemical and chemical laboratory. The system is not suited for these samples. Due to the open contact of the sample with the surroundings, samples may become contaminated. This may disturb the measurement.

Moreover, it is not possible to re-obtain valuable samples after the measurement without the risk of contamination.

The spectrophotometer is a very expensive measuring system. It comprises a measuring unit and a PC and consumes much space. The sample may quickly evaporate and easily become contaminated, because the surface area of the open drop of liquid has direct contact to the surroundings.

BRIEF SUMMARY OF THE INVENTION

Starting from this, the present invention is based on the objective to provide a device that is suited for the optical examination of small amounts of sample with high precision, using conventional optical measuring devices.

Further, a method is to be provided which permits the optical examination of particularly small amounts of sample.

The cuvette of the present invention comprises at least one measuring area on each one of two arms that are pivotally connected to each other, such that from a swung-apart condition, they can be swung together into a measuring position in which the two measuring areas have a distance from each other for positioning a sample between the measuring areas, and means for positioning the two arms in the measuring position in a cuvette shaft of an optical measuring device with a sample between the two measuring areas in a beam path of the optical measuring device that crosses the cuvette shaft.

According to one embodiment, a cuvette of the present invention comprises at least one measuring area on each one of two arms that are pivotally connected to each other, preferably by way of an articulation, such that from a swung-apart condition, they can be swung together into a measuring position in which the arms can be positioned in a cuvette shaft, and the two measuring areas face each other and have a distance from each other. As means for positioning, this embodiment has a form of the arms swung together in the measuring position that matches the cuvette shaft. This cuvette is adapted to the cuvette shaft by the form of the arms swung together, so that a sample held between the measuring areas is disposed in the beam path when the cuvette is put into the cuvette shaft. As a consequence, the arms of this cuvette are also designated as "adapter parts," or both arms together as "adapter" in the following.

According to another embodiment, a cuvette of the present invention comprises at least one insert with two measuring areas and an adapter for insertion into a cuvette shaft of an optical measuring device, and means of insert and adapter for detachably holding the at least one insert on the adapter, the measuring areas being in a distance from each other, for positioning a sample between the measuring areas in a beam path of the optical measuring device that crosses the cuvette shaft.

In this embodiment, the adapter has a shape matched to the cuvette shaft, so that a sample held between the measuring areas of the insert is disposed in the beam path when the insert is put into the adapter and the adapter is set into the cuvette shaft.

A preferred embodiment features means for positioning the two arms disposed in the measuring position in a standard cuvette shaft. A standard cuvette shaft in the spirit of the present invention has a rectangular, in particular square cross section.

According to one embodiment, it has a bottom area of 12.5 a 12.5 mm. According to a further embodiment, the beam path runs in a distance of 8.5 mm to 20 mm above the bottom of the cuvette shaft. According to a further embodiment, the beam path runs in a distance of 8.5 mm or 15 mm above the bottom of the cuvette shaft. The cross section of the cuvette, for instance the cross section of the swung together arms or the cross section of the adapter for receiving the insert, is matched to the cross section of the standard cuvette shaft. According to one embodiment, the measuring areas are positioned such in the cuvette that their centre has the above-mentioned distance of the beam path from the bottom of the cuvette shaft.

According to one embodiment, the cuvette has means for positioning the two arms disposed in the measuring position in different positions in a cuvette shaft. According to further embodiments, these are means for positioning in different heights and/or different horizontal positions in the cuvette shaft. The means may for instance be feet of the cuvette that can be drawn or screwed outward, or they may be realised by an asymmetrical arrangement of the measuring areas in connection with an arrangement of the cuvette in different rotational positions in the cuvette shaft. For instance, they serve for the adaptation to the height of the beam path of the measuring device, or for measuring different samples on the measuring areas of one cuvette in the same measuring device.

In the spirit of the present invention, a cuvette is a device which is destined to position samples for optical examinations. Thus, a cuvette of the present invention has not to be realised in a conventional manner as a vessel with an accommodation for liquids that is enclosed by bottom- and side walls, such a realisation being not excluded at all, however.

In the cuvettes of the present invention, a small volume of a liquid sample is positioned between the two measuring areas. A column between the two measuring areas is formed by the surface tension of the liquid, through which an optical measurement can be performed. The adapter serves to position the measuring areas in a preferably vertical alignment such in the cuvette shaft, that it can be measured in a conventional photometer or spectrometer without further alterations of the light path. For this purpose, the adapter is preferably matched to the dimensions of a standard cuvette shaft, so that it can be inserted like a standard cuvette. But however, the adapter can also be matched to a cuvette shaft with other dimensions than a standard cuvette shaft.

The insert and/or adapter may be realised for multiple use or as a consumable or disposable item for single use. The insert and/or the adapter may be made of one or plural plastics and/or of one or different materials. Insert and adapter can alternatively be fixedly connected, or consist of one single device, respectively.

The insert and/or the adapter is for instance made of metal (like aluminium or stainless steel, e.g.), and/or of one or plural plastics or hard plastics or soft plastics, respectively (for instance polystyrene, PVC, polypropylene, polyethylene). The measuring areas or insert parts that have the measuring areas are for instance made of transparent plastics (for instance Topas or polystyrene), quartz glass or another optically transparent glass (for instance BK 7). For measuring nucleic acids, a combination of an adapter of aluminium with measuring areas or insert parts, respectively, of quartz glass is well suited in particular.

Alternatively, the measuring areas may also be realised such that several samples can be arranged on them, for instance by corresponding surface shaping. The samples may be different or be applied on the measuring area as identical samples.

According to possible embodiments, the two measuring areas are arranged on two arms of an insert, of a pincette in particular, or on two adapter parts of an adapter realised as a collapsible device, by the aid of which a sample arranged between the two measuring areas can be aligned in the measuring direction. In this, the two measuring areas can be connected in one piece with the two arms or adapter parts, which on their turn can be connected with each other by being one piece. When the arms or adapter parts are swung apart, the measuring areas stand one towards the other such that a sufficiently great free space is provided for applying the liquid sample, for instance in the form of a drop. The sample can be applied to only one or to both measuring areas. By swinging the two arms or adapter parts together, it is achieved that the medium wets both measuring areas and a column of liquid is formed there between. Alternatively, the liquid may also be applied directly into a gap between the two measuring areas, so that a relative movement of the measuring areas towards each other can be omitted. For this purpose, the liquid can be put in between measuring areas that are movable with respect to each other and which were set to a suitable distance from each other. Further, for this purpose the liquid can be put between two measuring areas which have a stationary, fixed distance from each other.

Measurements with volumes from less than one micro-liter up to several micro-liters can be realised in one cuvette by distances of different magnitude between the two measuring areas. According to a preferred embodiment, the distances between the two measuring areas are dimensioned such that samples with volumes in the range of 0.2 to 5 micro-liters can be held there between. Further preferred, the distances between the measuring areas are dimensioned such that the volumes of the samples that can be held between them amount to about 1 to 3 micro-liters. Thus, the cuvette can be dimensioned for a certain volume, wherein the measuring areas can be held in the beam path only in a certain distance from each other.

Positioning a liquid sample on one of the two measuring areas, for instance of an insert or a collapsible device, can take place with the aid of a pipette. In this, the pipette can be set onto the measuring area with or without a guide device. After delivery of the necessary amount of sample, the arms of the pincette or collapsible device are swung together.

After application of the sample, an insert can be set into an adapter and it can be positioned in a vertical alignment in a cuvette shaft.

An insert of the present invention for an adapter that is insertable into a cuvette shaft of an optical measuring device has two measuring areas and means for holding on the adapter, the measuring areas being in a distance from each other, in order to position a sample between the measuring areas in a beam path of the optical measuring device that crosses the cuvette shaft.

The means for detachably holding the insert can be in particular contours or an outer geometry of the insert, respectively, which is matched to a contour or respectively geometry of the adapter, so that the insert can be joined to the adapter.

The insert of the present invention may advantageously have one or plural features of the insert of the cuvette of the present invention explained above, which comprises at least one insert and an adapter.

An adapter of the present invention for at least one insert having two measuring areas can be put into the cuvette shaft of an optical measuring device and has means for detachably holding the at least one insert, the measuring areas being in a distance from each other, in order to position a sample between the measuring areas in a beam path of the optical measuring device that crosses the cuvette shaft.

The adapter of the present invention may advantageously have one or plural features of the adapter of the cuvette of the present invention explained above, which comprises at least one insert and an adapter.

The means for detachably holding the adapter can be in particular a contour or respectively geometry of the adapter, which is matched to a contour or respectively geometry of an insert, so that the adapter can be joined to the insert.

A collapsible device of two arms or respectively adapter parts that are connected by an articulation has the shape of a common commercial cuvette when the two adapter parts are swung together. The measuring areas can be present in particular on replaceably installed insert parts of quartz glass or plastics. Further, they may be connected to the arms or respectively adapter parts as being one piece and/or in a not detachable fashion. For instance, the arms with the measuring areas are made as one piece of plastics. In this, the arms are connected to each other preferably as being one piece, for instance via a film hinge. Insert parts of quartz glass or replaceable insert parts of plastics can in particular be present in cuvettes for multiple use. Collapsible cuvettes for multiple use may in particular feature arms or respectively adapter parts of metal. An arm or respectively an adapter part of metal or of another material that is not optically transparent (for instance of an opaque plastics) can be realised as a stop for limiting the light passage through the measurement volume.

A collapsible cuvette can be made of plastics or another material for multi-use or as a disposable item for single use. The two adapter parts can be connected articulately with each other via a film hinge, or each may have articulation parts which are mutually connected to a joint. The adapter parts can serve as stops for shielding the measurement volume against excess light. For this purpose, the adapter parts may consist entirely or partly of coloured plastics, or they may wear light-impermeable coatings. For instance, the collapsible cuvette has adapter parts of UV-impermeable plastics and inserts of UV-transparent plastics.

According to one embodiment, there are means for detachably locking the two adapter parts in the measuring position. These may be incorporated magnets, in adapter parts of metal in particular. Elastic catching hooks that co-operate with catching edges may exist in adapter parts of plastics in particular. The catching hooks and catching edges can be made in one piece with the adapter parts of plastics.

In all the variants of the present invention mentioned above, the beam path of the optical measuring device may run crosswise through the measuring areas, for which purpose the measuring areas or respectively the insert having the measuring areas are realised as being transparent or clear or optically diaphanous, respectively. According to another embodiment, the beam path of the optical measuring device runs in parallel to the measuring areas through open sides of the distance region between the measuring areas. In this case, the measuring areas may also be made light-impermeable. Even though the beam path does not run across the measuring areas in this embodiment, they are designated as "measuring areas", because they position the drop for the measurement in the beam path.

In principle, measuring areas may have a curved one or another shape. According to a preferred embodiment, the measuring areas are planar. When the measuring areas are disposed on the side of an insert part (for instance, of a platelet) or respectively of a wall, both sides of the platelet or respectively the wall are preferably planar.

In principle, the planar measuring areas may have any arbitrary alignment to each other. For instance, they may be aligned at an angle to each other. According to a preferred embodiment, the measuring areas are disposed with surfaces parallel to each other. This plane-parallel arrangement of planar measuring areas serves in particular for the passage of the beam path through the measuring areas without disturbing deflection of the light beam.

In principle, the measuring areas may have different alignments with respect to each other, for instance such that the measuring areas occupy angles against each other in all the three spatial axes. According to a preferred embodiment, the measuring areas are disposed such that they cover up each other. Preferably, the measuring areas are present on plane-parallel platelets in an arrangement so as to cover up each other.

According to one embodiment, the distance of the measuring areas from each other is 5 mm or less in the measuring position. At the mentioned distance, many of the liquid samples to be examined are held between the measuring areas due to capillary forces. The distance is preferably 0.1 to 2 mm. Particularly preferred is a distance of about 1 millimeter.

According to a method of the present invention for optically examining small amounts of liquid, two drops of liquid are applied to two preferably planar measuring areas, the drops are brought into contact with each other by drawing the two measuring areas near to each other, so that the drops coalesce into one single drop, and this drop is subjected to an optical measurement.

By applying a reduced measurement volume to both measuring areas, and the subsequent positioning or drawing together of the areas, a volume reduction may be achieved. Namely, the added height of two drops with half the volume is greater than the height of one single drop with the whole volume. Thus, wetting both measuring areas can be achieved with a smaller volume also.

According to a further variant, in a method of the present invention for optically examining small amounts of liquid, two measuring areas arranged in a distance from each other are simultaneously wetted with a liquid sample, so that the drop is spanned out between the measuring areas through its surface tension, and this drop is subjected to an optical measurement.

This method of positioning the sample amount upon simultaneous wetting of both measuring areas directly when the sample is applied results also in a reduction of the necessary amount of sample. A pipette may be used in order to position the sample. Guiding the pipette point before and after the pipetting process may favour this effect.

In all the variants of the present invention, safe and handling-friendly positioning of drops can be facilitated by guiding the pipette point when picking up and/or delivering the liquid.

The cuvette of the present invention is preferably dimensioned such that it fits into a standard cuvette shaft as a standard cuvette. But it may also be made such that it fits into a cuvette shaft of other conventional or future optical measuring devices.

BRIEF DESCRIPTION OF THE SEVERAL VIEWS OF THE DRAWINGS

In the drawings shows:

FIG. 13.1 a variant of the adapter with a recess for inserting a pipette point with arms swung apart, in a perspective view;

FIG. 14.1 the same adapter with arms swung together in a perspective view;

FIG. 14.2 the same adapter with arms swung together in a side view;

DETAILED DESCRIPTION OF THE INVENTION

Figure 1:
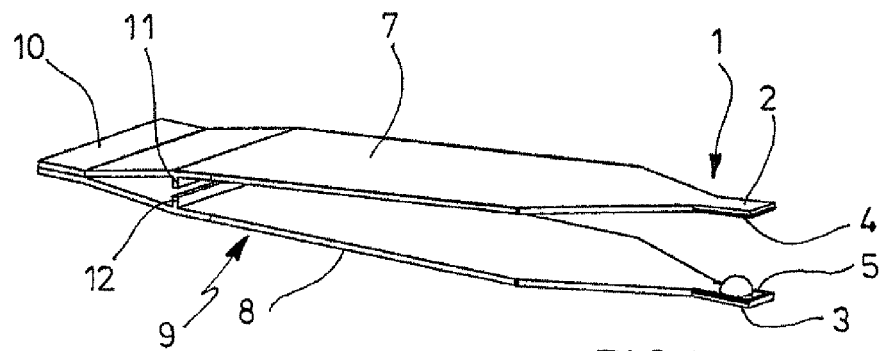
FIG. 1 a pincette with planar measuring areas at the free ends and opened arms, in a perspective view slantwise from the side.
Figure 2:
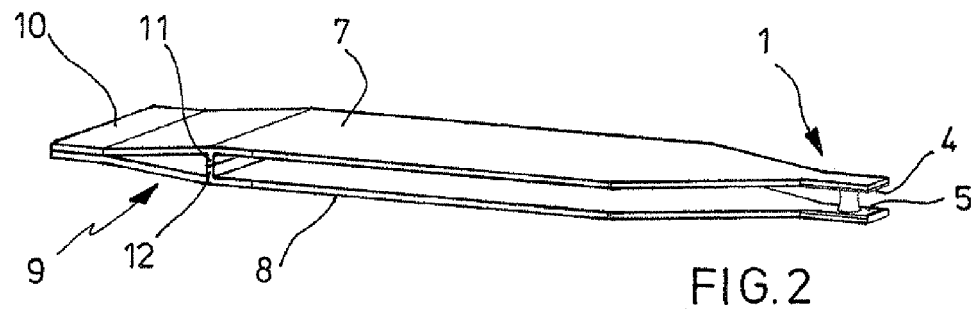
FIG. 2 the same pincette with arms swung together, in the same perspective view.
Figure 3:
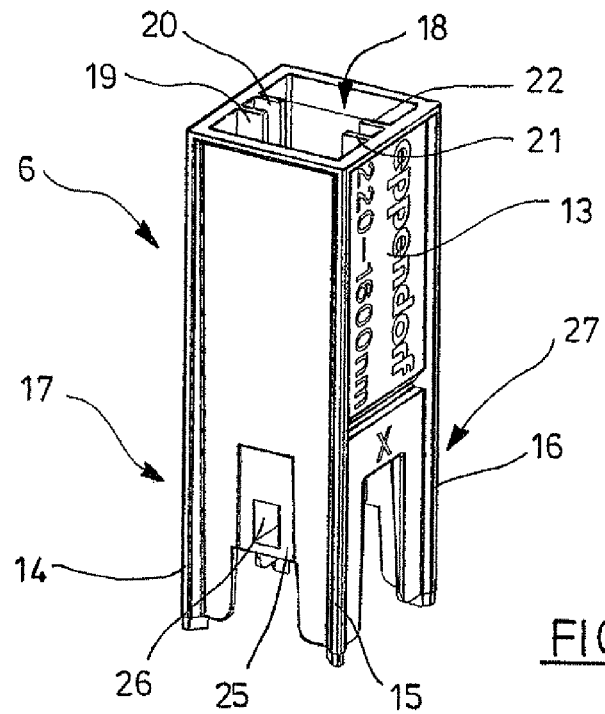
FIG. 3 an adapter with an accommodation for the pincette, in a perspective view slantwise from the topside and from the side.
Figure 4:
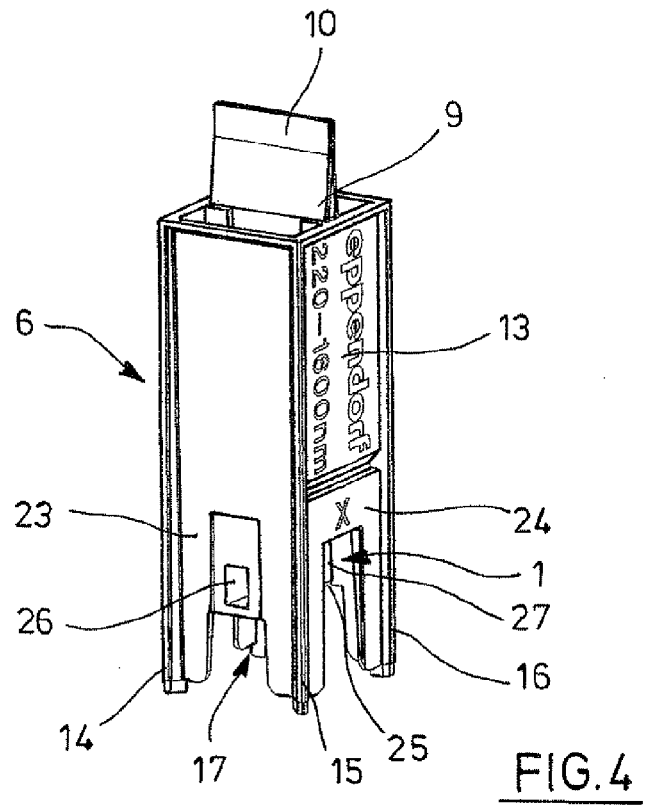
FIG. 4 the same adapter with inserted pincette, in a perspective X-ray image.
Figure 5:
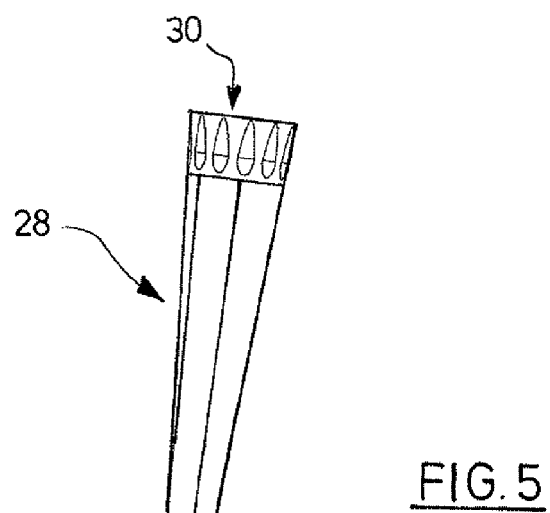
FIG. 5 a pipette point with planar measuring areas on the lower end, in a perspective view slantwise from the downside and from the side.
Figure 6:
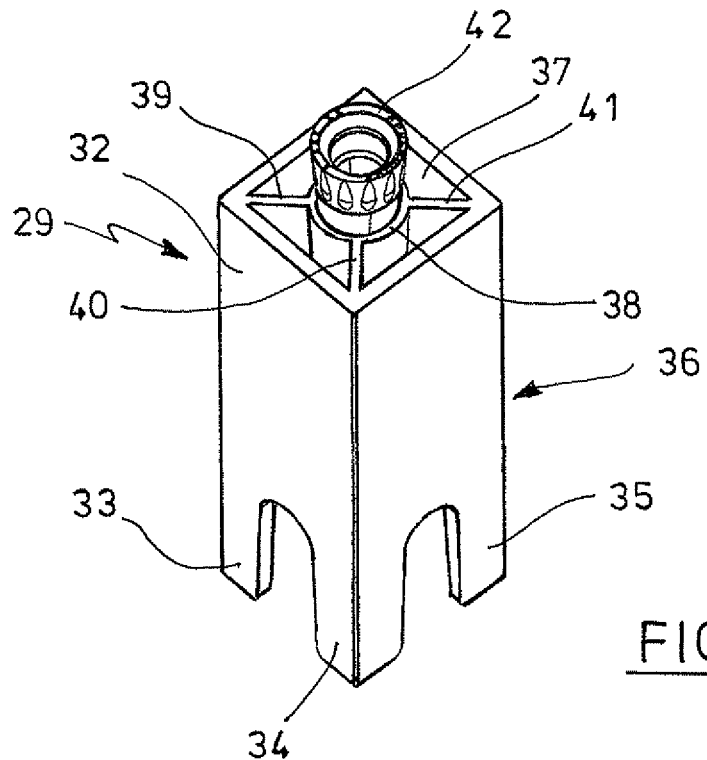
FIG. 6 an adapter with an accommodation and the pipette point inserted therein, in a perspective view slantwise from the topside and from the side.
Figure 7:
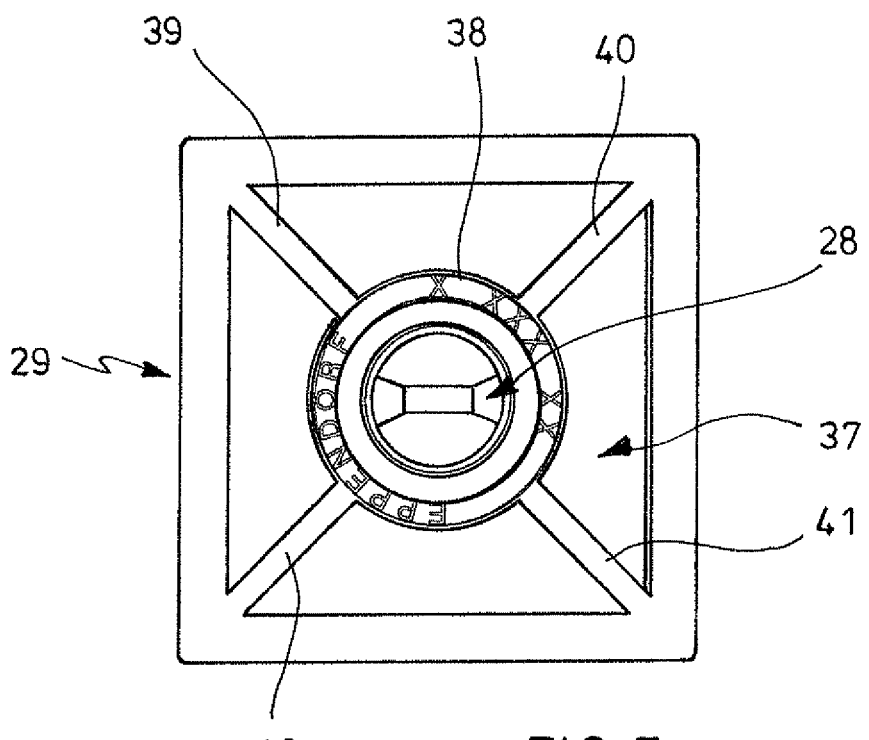
FIG. 7 the pipette point being inserted into the adapter, in a top view.
Figure 8:
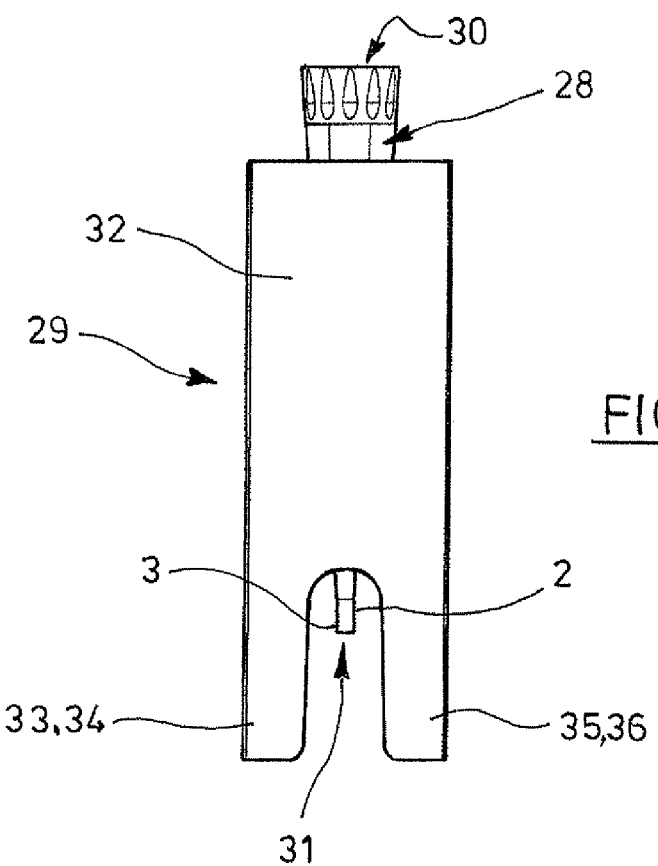
FIG. 8 the pipette point being inserted into the adapter, in a side view.
Figure 9:
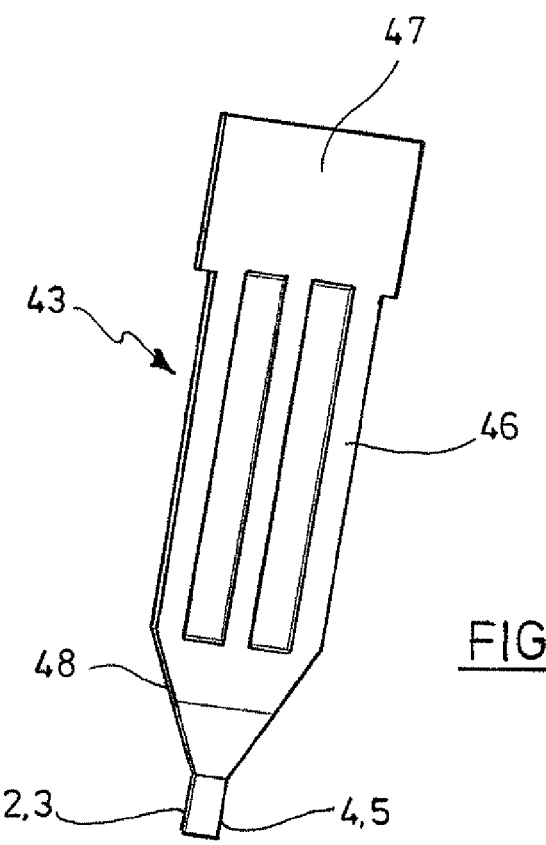
FIG. 9 a slide with a planar measuring area, in a perspective view slantwise from the topside and from the side.
Figure 10:
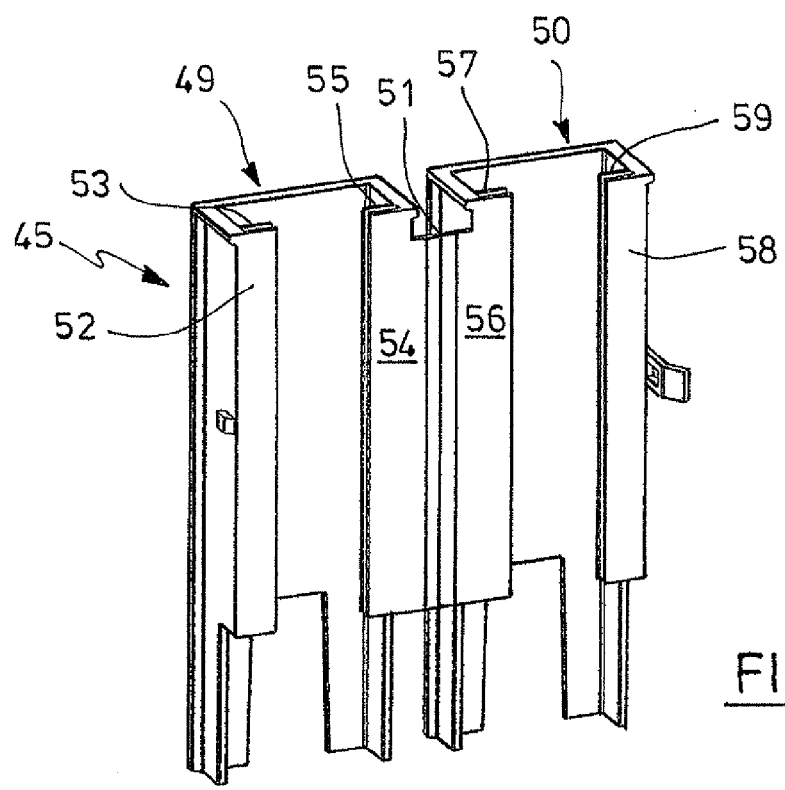
FIG. 10 an adapter for accommodating two slides in the opened condition, in a perspective view slantwise from the topside and from the side.

While this invention may be embodied in many different forms, there are described in detail herein a specific preferred embodiment of the invention. This description is an exemplification of the principles of the invention and is not intended to limit the invention to the particular embodiment illustrated In the following, the designations "upside" and "downside" refer to that orientation which the corresponding parts of the device have when they are arranged in a cuvette shaft of a photometer or spectrometer.

The cuvette shown in FIGS. 1 to 4 consists of at least two parts.

A device 1 consists of two platelets 2, 3 with planar measuring areas 4, 5 on the inner sides, and an adapter 6 for positioning the device 1 in a conventional photometer, spectrometer or the like.

In the example, the platelets 2, 3 of the device 1 are arranged on the free arms 7, 8 of a pincette 9. In their lower region, the arms 7, 8 are bevelled towards the platelets 2, 3. The arms 7, 8 are preferably fixedly connected to each other on the upper ends at 10. The arms 7, 8 can be elastically swung together. Swinging the arms 7, 8 together is limited by the spacer parts 11, 12 arranged on the inner sides of the arms 7, 8 in the form of two ribs running crosswise to the arms, preferably near to the measuring areas.

The adapter 6 itself has the cuboid-shaped outline of a standard cuvette. In its upper region, it is closed all around, and at the bottom side it has four feet 14 to 17.

The adapter 6 has a cavity 18 in its interior, two parallel guide rails 19, 20, 21, 22 for the pincette 9 being arranged in the interior on each of two opposing side walls. The pincette 9 can be inserted into the guiding mechanism formed by the guide rails 19 to 22 when the arms are swung together according to FIG. 2.

At the downside, the guide rails 19 to 22 are limited by limitation walls 23, 24 inclined towards the inside, whose inclination corresponds to the inclination of the bevels of the arms 7, 8 of the pincette 9. At the inside, the limitation walls 23, 24 project from the side walls which bear the guide rails 19 to 22.

A box-like bottom part 25 is inserted onto the lower borders of the limitation walls 23, 24. This part has passage openings 26, 27 on opposing front surfaces.

Thus, the construction of the adapter 6 corresponds essentially to the cuvette according to the German patent DE 198 26 470 C1, U.S. Pat. No. 6,249,345, the disclosure of which is incorporated herein by reference. The deviations from the known constructions are that the inner sides of the side walls are provided with the guide rails 19 to 22, and that the box-like bottom part 25 has passage openings 26, 27.

The pincette 9 may be realised as a disposable item. The adapter 6 may also be a disposable item or it may be re-usable. Pincette 9 and adapter 6 are preferably made of plastics.

A small volume of the liquid to be analysed is positioned between the optically transparent measuring areas 4, 5 of the device 1. The adapter 6 serves to position subsequently the device 1 having the planar measuring areas 4, 5 in a vertical alignment such in a cuvette shaft that it can be measured in a conventional photometer or respectively spectrometer without further change of the light path.

The pincette 9 may feature an introducing aid, which permits a simple "filling" of the measuring areas 4, 5. In the opened condition, the arms 7, 8 of the pincette stand towards other such, that a sufficiently large space is provided for applying the sample, for instance in the form of a drop, onto one of the planar measuring areas 4,5. By pushing together the two arms 7, 8, the planar measuring areas 4, 5 on the ends of the arms 7, 8 are moved towards each other, so that the drop wets both measuring areas 4, 5. In this, the planar measuring areas 4, 5 can be shaped and/or coated such that the direction of spreading of the medium towards the measurement direction is favoured, and that when it is overdosed, it can escape only in one direction, for instance towards the topside. By the two spacer parts 11, 12, preferably situated near to the planar measuring areas 4, 5, the arms 7, 8 are positioned such that a defined optical layer thickness between the measuring areas 4, 5 is generated. Measurements with volumes from one micro-liter up to several micro-liters can be realised in one adapter 6 by means of different pincettes 9 having different layer thicknesses.

In addition, the pincette 9 may contain a locking function which permits the user to leave the pincette from his/her hand in the closed state, in which the spacer parts 11, 12 sit close to each other.

Furthermore, the pincette may contain alignment devices in addition, which align the measuring areas 4, 5 in parallel.

In its closed condition, the pincette 9 is inserted into the guide rails 19 to 22 of the adapter 6, until the bevels of the arms 7, 8 abut against the inclined limitation walls 23, 24 of the adapter. In this position, the platelets 2, 3 are arranged vertically in the adapter 6, and are directed towards the passage openings 26, 27 with their outer sides. The pincette 9 can be kept in the closed condition by the guide rails 19 to 22.

When the adapter 6 is arranged in the cuvette shaft of a photometer or spectrometer, the passage openings 26, 27 are arranged in the beam path of the measuring optics, so that the same can be used for the optical measurement of the sample between the measuring areas 4, 5.

The adapter 6 can be realised such that any leakage of the liquid sample upon mistreatment, at shocks for instance, is prevented. Moreover, it can have the features of a stop, by which an universal utilisation not depending on the type of the spectrometer is possible. The adapter 6 can be realised as a disposable item like a cuvette, but replacement is necessary only in the case of mistreatment.

The cuvette of FIGS. 5 to 8 is not subject matter of the present invention, it is described only for illustrating the claimed invention.

The cuvette according to FIGS. 5 to 8 consists of at least two components, namely of a measurement point 28 and an adapter 29. The measurement point 28 has an upper end with an upper opening 30, by which it can be clamped onto a fastening neck of for instance a currently marketed pipette. Further, it has a bottom end with a bottom opening 31. This bottom opening 31 is limited by a device 1, comprising two transparent platelets 2, 3 having planar and preferably plane-parallel measuring areas 4, 5 at the inner sides. The distance region between the platelets 2, 3 is laterally closed, so that the distance region is open only on the bottom side at 31.

A continuous channel is formed in the measuring point 28 between the upper opening 30 and the lower opening 31. At the outside, the measuring point 28 has a form that tapers from the topside to the bottom side.

The adapter 29 is also box-like and matched to a standard cuvette shaft. In the upper region 32, it is closed on the circumference, and on the downside it has four feet 33 to 36. In the interior, the adapter 29 has a cavity 37, in which an accommodation 38 is arranged. The accommodation 38 is matched to the outer contour of the measurement tip 28. At the inside, the accommodation 38 is supported on the walls of the adapter 29 via radially running ribs 39, 40, 41, 42.

The measuring point 28 can be put up onto a fastening neck of e.g. an usual commercial pipette, like a conventional pipette point, by way of which the medium to be measured can be sucked in between the platelets 2,3. In doing so, the medium wets the planar measuring areas 4, 5. Measuring reservoirs of different magnitude for measurements having volumes of less than one micro-liter up to several micro-liters or different layer thicknesses, respectively, can be realised in one cuvette by way of different measuring points 28 with different distances between the measuring areas 4, 5. In embodiments for the measurement of very small volumes in particular, the sample to be measured can be drawn between the plates 2, 3 by the capillary forces already. Picking up the sample with the aid of for instance a commercially available pipette is then no more necessary.

The filled measuring point 28 is put into the adapter 29 with the aid of a pipette. The shape of the accommodation 38 is matched to the shape of the measuring point 28, such that the inserted measuring point is arranged with the platelets 2, 3 in the free spaces between the feet 33 to 36. The cuvette 29 can then be put into a cuvette shaft with the measuring point 28 being put in, so that the light path of the optical measurement device runs between opposing free spaces between the pairs of feet 33, 34 and 35, 36 and crosswise through the two platelets 2, 3 and the sample situated therein. Picking up the sample is favoured by hydrophilic surfaces.

The adapter 29 can be realised such that leakage of the liquid to be measured upon wrong handling—at too strong a shock for instance—is prevented. Furthermore, it can serve as a guiding mechanism for the correct alignment of the planar measuring areas 4, 5 with respect to the measurement direction of the photometer. Further, it may have the nature of a stop, by which a universal utilization independent of the spectrometer's type is possible.

Measuring point 28 and adapter 29 can each be realised as consumables. The measuring point 28 can be replaced after each measurement. Replacement of the adapter 29 can be limited to cases of wrong treatment.

The following two realisation examples comprise two collapsible adapter parts, which are preferably captively connected to each other via an articulation. In a collapsed condition, the adapter parts form an adapter, with the dimensions of e.g. a standard cuvette. The articulation may be attached on the short or on the long side of the device. Swung apart, the sample to be measured is applied to only one or to both measuring areas.

The cuvette according to FIGS. 9 to 12 comprises two plate-shaped sample carriers ("slides") 43, 44 and an adapter 45. The sample carriers 43, 44 are identical. The have an enlarged grip and path stop 47 on the upper end of a strip-shaped centre part 46. At the downside, the strip-shaped centre part 46 tapers conically at 48. On the lower end, each of the slides 43, 44 has a platelet 2, 3 with the planar measuring area 4 respectively 5, preferably on one side.

The adapter 45 comprises two adapter parts 49, 50, which are articulatedly connected to each other via a film hinge 51. In a collapsed condition, the adapter parts 49, 50 according to FIG. 12 form an adapter 45, whose form corresponds essentially to that of the adapter 6 according to FIGS. 3 and 4. However, in difference to the adapter 6, the adapter 45 has a complete guiding mechanism consisting of four guide rails 52 to 55 and 56 to 59 in each one of both adapter parts 49, 50. The adapter 45 and the slides 43, 45 are preferably made of plastics.

Figure 11:
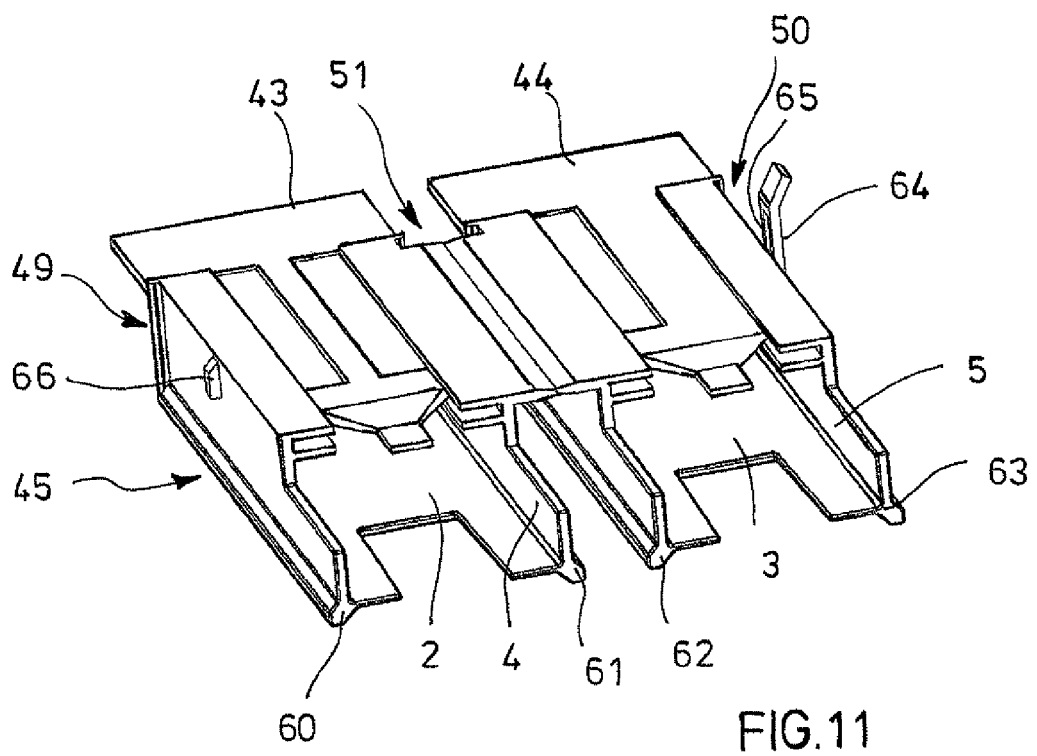
FIG. 11 the adapter equipped with two slides in an unfolded condition, in a perspective view slantwise from the downside and from the side.

According to FIG. 11, two slides 43, 44 are inserted into the guiding mechanisms 52 to 55 and 56 to 59, until the grip and path stop 47 finds rest on the upper border of the two adapter parts 49, 50. In this position, the platelets 2, 3 are disposed in recesses between feet 60, 61 of the adapter part 49, and 62, 63 of the adapter part 50. Further, a catch lock of the slides 43, 44 with the guiding mechanisms 52 to 55 and 56 to 59 can be provided.

Then, one drop of the liquid to be measured is applied to the planar measuring area 4. Thereafter, the two adapter parts 49, 50 are swung together, whereby the liquid comes into contact with the measuring area 5.

The collapsed adapter parts 49, 50 are locked with each other by way of a catching hook 64 having a catching recess 65 on the adapter part 50, and a catching projection 66 on the adapter part 49. In this, the catching hook 64 is pushed onto the catching projection 66 with its catching recess 65. By actuating the catching hook 64 in the opposite direction, the locking can be released.

Figure 12:
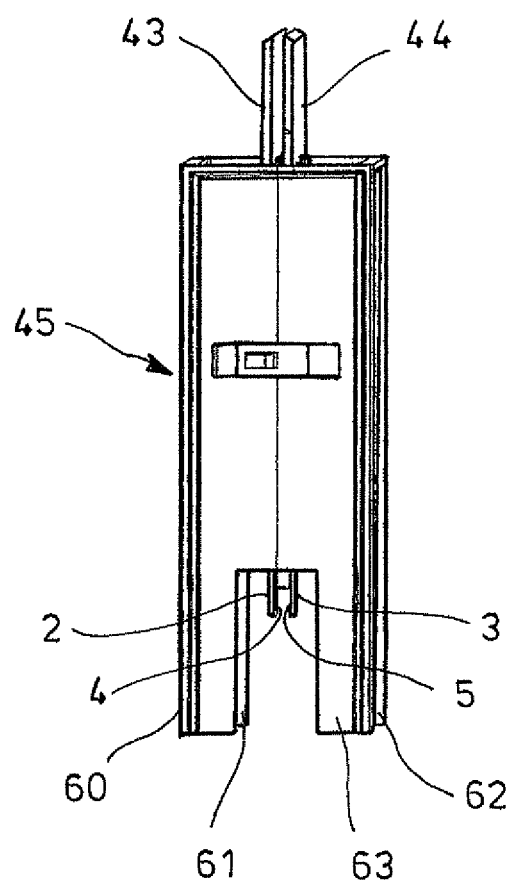
FIG. 12 the adapter equipped with the slides in the collapsed condition, in a perspective view on two sides.

According to FIG. 12, the closed adapter 45 can be put into a standard cuvette shaft, wherein the beam path of the optical measuring device crosses the two platelets 2, 3 through the recesses between the feet 60, 61 and 62, 63.

In the cuvette according to FIGS. 9 to 12, the arms or respectively adapter parts 49, 50 are articulated to each other along a long side. In the cuvette according to FIGS. 13 and 14, the arms or respectively adapter parts 67, 68 have an articulated joint 69 along a transversal axis.

For this purpose, the adapter part 67 has a plate-shaped base part 70, which has two bridges 71, 72 at its upper region on one side at the outside. Bearing eyes 73, 74 of the revolution joint 69 are arranged in the bridges 71, 72.

In principle, the adapter part 68 consists of a plate-shaped carrier part 75, which is connected to one end of a connection arm 76, which carries a bearing block 77 at its other end. The bearing block 77 is arranged between the legs 71, 72, an axis or shaft 78 being guided through a central passage bore of the bearing block 77 and being held in the bearing eyes 73, 74 on both ends.

The base part 70 and the carrier part 75 have passage openings 79, 80, which are in true alignment with each other in the collapsed condition of the adapter parts 67, 68. On the inner sides of the passage openings 79, 80 sit plate-shaped insert parts 81, 82 with planar measuring areas 83, 84 on their inner sides.

Preferably, the base part 70 and the carrier part 75 each have magnets 85, 86, 87 and 88 and 89, 90, 91 and, each inserted in the inside, which sit pairwise close to each other in the collapsed condition. Further, a centring pin 93 projects from the base part 70, to which is associated a centring accommodation 94 of the carrier part 75.

It is advantageous to adjust the distance between the measuring areas 83, 84 via the magnet pairs in the manufacture of the cuvette. This may for instance be achieved by setting the magnets 85 to 92 into adhesive beds. These are allowed to harden when the cuvette is in a closed condition, the correct alignment of the magnets 85 to 92 being made sure by a locating piece that is inserted between the measuring areas 83, 84. At option, the adhesive bed of one magnet 85 to 92 at a time of each pair can be hardened already before closing. In order to design the system without remaining degrees of freedom, but not in an overdetermined fashion, it is advantageous to use three pairs of magnets. In addition, for the same reason it is advantageous to design the revolution joint 69 of the cuvette floatingly, i.e. with clearance, with respect to the axis vertical to the measuring areas 83, 94.

A sample can be applied to one or both planar border surfaces 81, 82 in the opened condition of the adapter. After collapsing the adapter parts 67, 68, the adapter is insertable into a standard cuvette shaft. The light path of the optical measuring device passes through the passage openings 79, 80, the transparent platelets 81, 82 arranged behind them and the sample situated there between.

The insert parts 81, 82 are for instance made of UV-permeable quartz glass or UV-permeable plastics. As the case may be, they are provided with a special surface structure.

The borders of the passage openings 80, 81 form stops, which effect that the measuring light of the photometer or spectrometer irradiates only through the sample. The adapter parts 67, 68 are preferably made of plastics.

The adapter parts 67, 68 may be made of another material, of metal for instance, in particular when they are destined for re-use. In a further variant, the adapter parts 67, 68 may consist of the same plastics like the insert parts 81, 92, and as the case may be, they may be produced inseparably as one single injection moulded object.

In particular, the cuvette can be made such that a gap remains after collapsing it, via which the region between the measuring areas 83, 84 can be inspected. This can be used in order to fill the cuvette in its closed condition. In order to facilitate filling, the gap can be enlarged with a recess in the direction towards the measuring areas.

Figure 13:
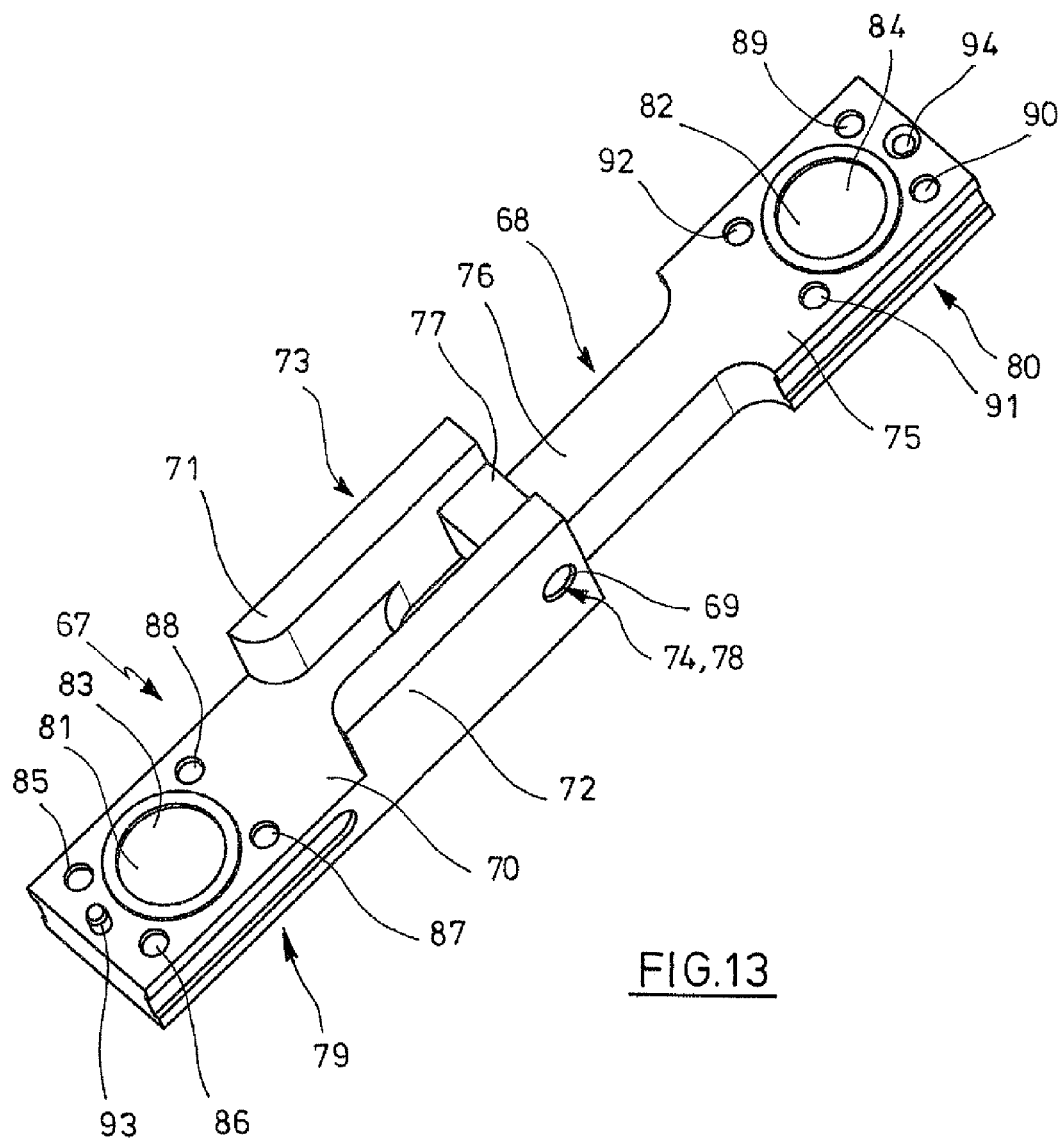
FIG. 13 an adapter equipped with insert parts having planar measuring areas, the adapter parts being swung apart, in a perspective view slantwise from the downside and from one side.

Another variant, which permits to fill the cuvette in the closed condition, is shown in FIGS. 13.1, 14.1 and 14.2. When filling the cuvette in the closed condition, both measuring areas 83, 84 are wetted at the same time. This has the advantage that a smaller volume is needed in order to produce a liquid bridge between the measuring areas 83, 84. Besides to this, the evaporation of the sample during the handling can be prevented by doing so.

Figure 14:
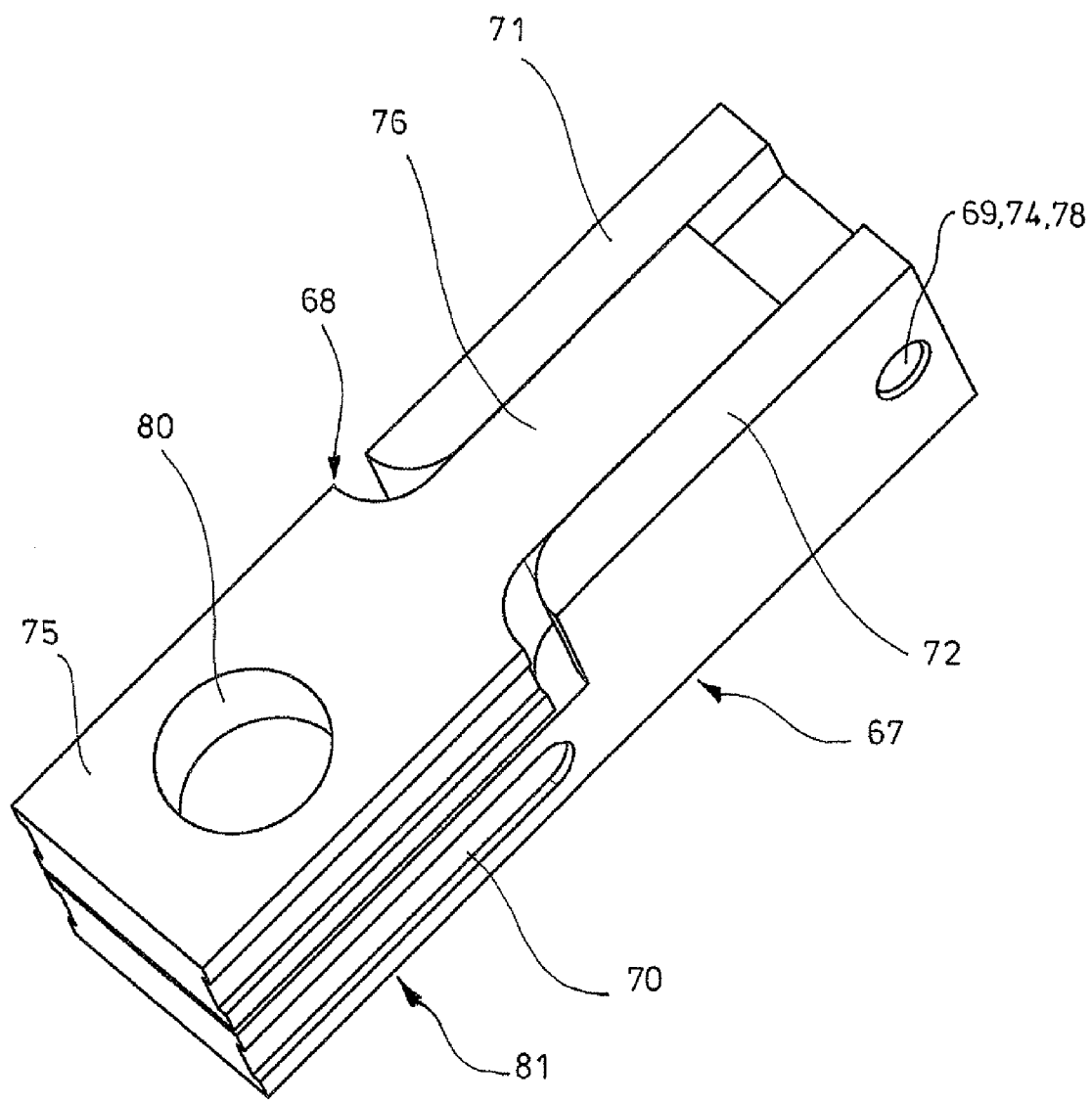
FIG. 14 the same adapter with adapter parts swung together in the same perspective view.

In FIGS. 13.1, 14.1 and 14.2, those elements that correspond to elements of the embodiment of FIGS. 13 and 14 are designated with the same reference signs, but which are indicated by a superscripted dash (').

In order to fill it in the closed condition with the aid of a pipette, the embodiment of FIGS. 13.1, 14.1 and 14.2 has a recess 125 in the arm 67 which extends on the free end of the arm 67' from out its outer side 126 up to the measuring area 83'. The slot-like recess 125 is shaped and dimensioned such that the lower end of the pipette point 127 fits into it and is laterally guided therein. Further, the insert part 81' is arranged somewhat nearer to the revolution joint 69' than the insert part 82', so that the sample can be metered directly onto the measuring area 84' and into the interstice between the measuring areas 83', 84' by way of the pipette point 127.

In this embodiment, the insert parts 81, 82' are made strip-shaped and detachably or fixedly connected to the arms 67', 68'. The revolution joint 69' is made as a floating hinge, for instance by arranging the axle or shaft 78' either in a passage opening with oversize of the bearing block 77' and pressing it into the bearing eyes 73', 74', or by pressing it into the passage bore and arranging it in the bearing eyes 73', 74' that have oversize. Further, this embodiment has three pairs of magnets 85', 86' and 87' and 89', 90' and 91' for locking the arms 67', 68' in the measuring position.

Figure 15:
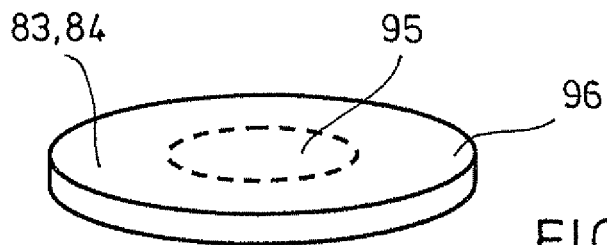
FIG. 15 insert part with planar measuring area having liquid-wetting and liquid-repellent zones, in a view slantwise towards the planar measuring area and towards the side.
Figure 16:
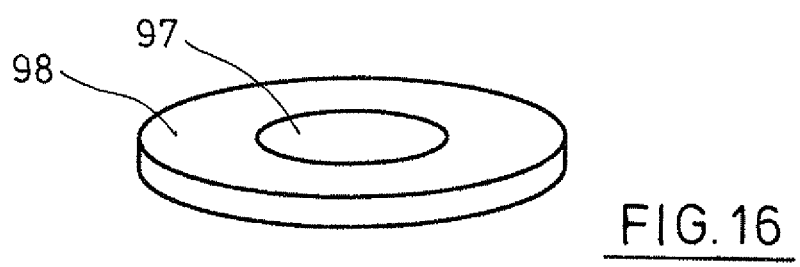
FIG. 16 the same insert part in a perspective view towards the opposing planar outer side.
Figure 17:
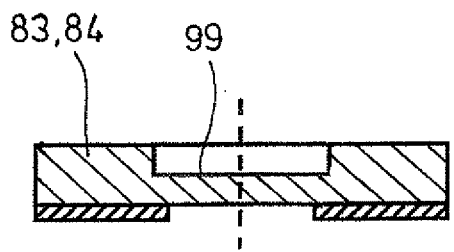
FIG. 17 planar measuring area with recess, in a longitudinal section.
Figure 18:
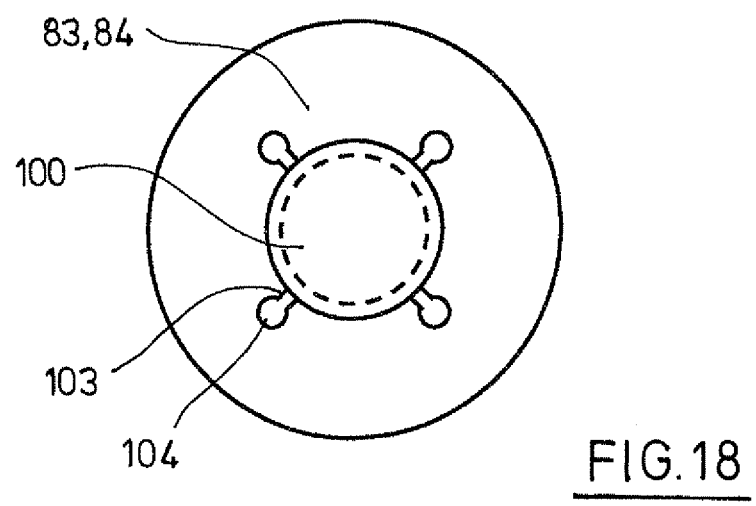
FIG. 18 planar measuring area with several overflow chambers in a top view.
Figure 19:
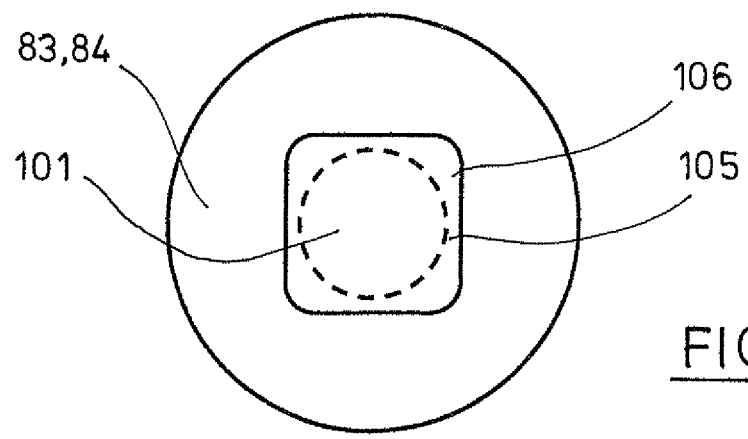
FIG. 19 planar measuring area with one overflow chamber in the top view.
Figure 20:
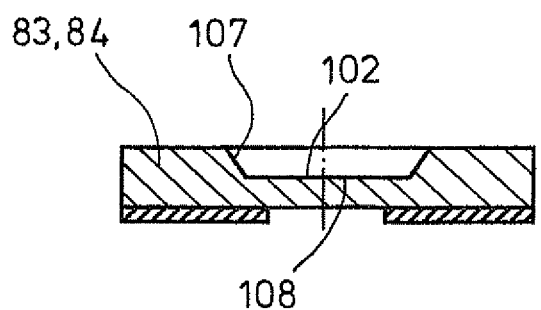
FIG. 20 planar measuring area with liquid-wetting centre region and liquid-repellent border surfaces in a longitudinal section.

According to FIGS. 15 and 16, the optically transparent measuring areas 83, 84 are realised so as to have a central liquid-wetting surface portion 95, around which there is a liquid-repellent surface portion 96. The liquid-wetting and liquid-repellent properties of the regions 95, 96 can be produced by coatings. Between the two surface portions 95, 96 there is no mechanical edge which would disturb when the measuring areas 83, 84 are being cleaned. The measuring areas 83, 84 are cleaned starting from the surface portion 95 and towards the surface portion 96, so that no residual contaminations remain in the central surface portion 95.

A light-permeable surface portion 97 corresponds to the liquid-wetting surface portion 95, and a light-impermeable surface portion 98 on the outer side of the insert part 83, 84 corresponds to the liquid-repellent surface portion.

The surface portions 95, 96 limit the spreading of the liquid sample on the measuring areas 83, 84. On the liquid-repellent respectively hydrophobic surface portion, the drop of liquid has a great contact angle point. Due to this, it projects far above the measuring areas 83, 84. However, in the liquid-wetting respectively hydrophilic surface portion 95, the drop is retained or anchored, respectively. Due to this, there arise no flat, but approximately semi-globular drops of liquid, so that when collapsing the adapter parts 67, 68, a drop that is applied to a measuring area 83 or 84 securely wets the other measuring area 84, 83, or other drops applied to both measuring areas 83, 84 securely unite with each other. As a consequence, there arises a defined column of liquid, and through this a defined measurement path or layer thickness, respectively.

The platelets 2, 3 of the remaining realisation examples can be realised correspondingly on the measuring areas 4, 5 and the outer sides.

In the realisation example according to FIGS. 17 to 20, differently shaped deepenings 99, 100, 101, 102 are arranged in the measuring areas 83, 84. The deepenings 99 to 102 accommodate samples and limit the spreading thereof on the measuring areas 83, 84. According to FIGS. 18 and 19, excess amount of sample can escape into reservoirs 104 via radial channels 103, or into an overflow chamber 106 via an overflow edge 105. In the realisation example of FIG. 20, the deepening 102 is conically enlarged towards the outside. In addition, the border surface 107 that limits the extension can be liquid-repellent, and the base surface 108 liquid-wetting, so that the drop projects from the measuring area 83, 84 as far as possible.

In order to limit the drop spreading, a planar pedestal having a small surface area can also be arranged on the measuring area 83, 84. The planar pedestal prevents the spreading of the drop due to its surface tension. This results in an increase of the drop height, and a reduction of the necessary amount of sample can be achieved.

The form of the measuring areas according to FIGS. 17 to 20 or with a pedestal can be realised in all embodiments.

Figure 21:
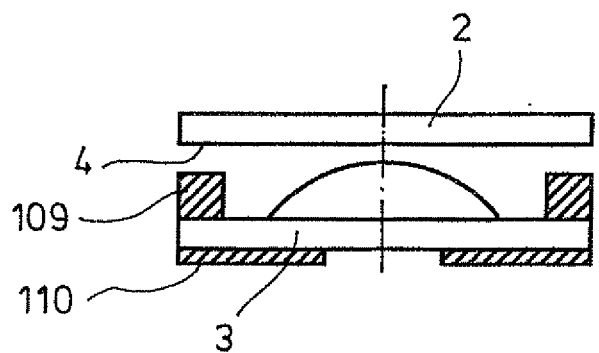
FIG. 21 planar measuring areas with one drop put up there before drawing the measuring areas together, in a longitudinal section.
Figure 22:
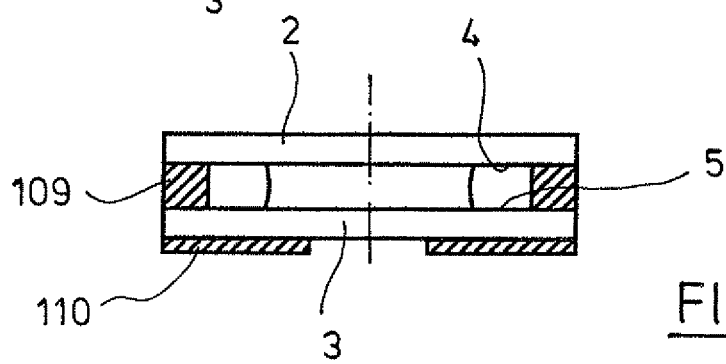
FIG. 22 the same measuring areas after drawing together, in a longitudinal section.

According to FIGS. 21 and 22, the thickness of the layer between the two measuring areas 4, 5 can be defined by a spacer ring 109. A stop 110 is applied as a coating on the outer side of the platelet 3.

In this example, a drop is applied only to measuring area 5, which wets the measuring area 4 upon close contact with the spacer ring 9.

Figure 23:
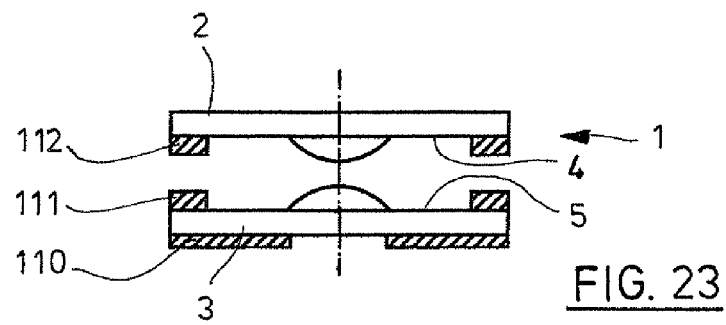
FIG. 23 two planar measuring areas with two drops put up there before drawing the measuring areas together, in a longitudinal section.
Figure 24:
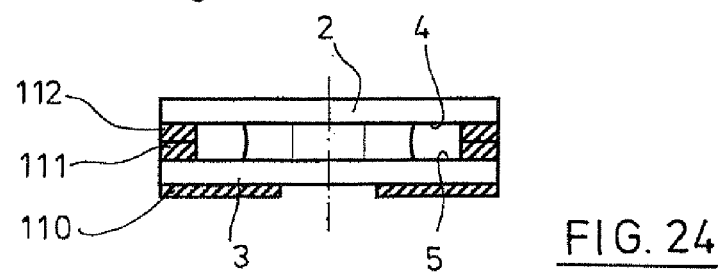
FIG. 24 the same measuring area after drawing together, in a longitudinal section.

In the realisation example according to FIGS. 23 and 24, spacer rings 111, 112 are assigned to both measuring areas 4, 5, which come into contact with each other when the device is closed. In this example, the layer thickness is defined by both spacer rings 111, 112. Further shown is the application of drops onto both measuring areas 4, 5, which coalesce when the device 1 is closed.

Figure 25:
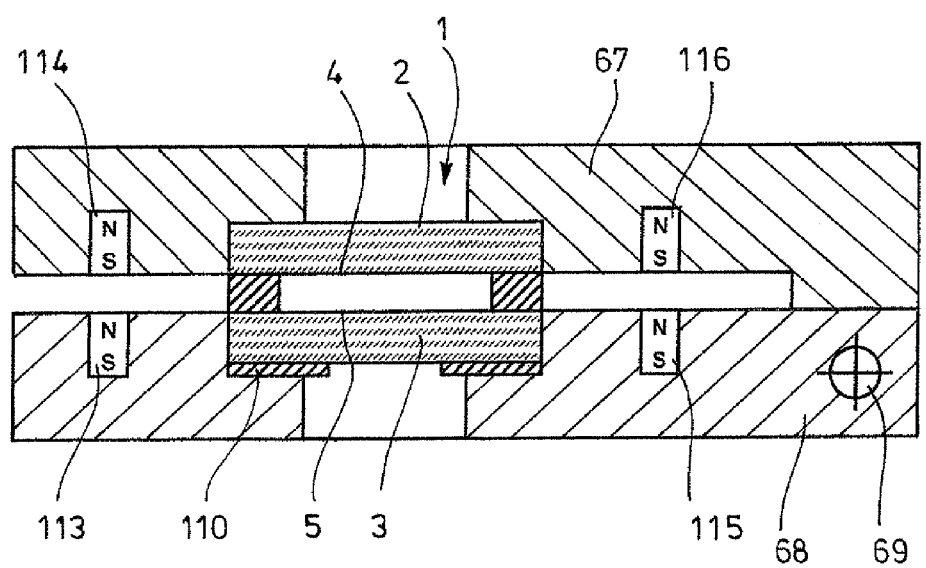
FIG. 25 magnetic locking of two measuring areas in the measuring position in a longitudinal section.

The realisation example of FIG. 25 differs from that according to FIGS. 21 and 22 in that the defined layer thickness is preferably ensured by magnetic forces from magnets 113, 114, 115, 116, whose unlike poles are arranged in a short distance from each other when the device 1 is closed. The magnets 113 to 116 are integrated into device components (for instance adapter parts 67, 68) of the cuvette, which accommodate the inserts 2, 3.

In order to ensure the plane-parallel alignment of the measuring areas 4, 5, a hinge 69 that is formed between the device components 67, 68 can be made to float, so that the system is not geometrically overdetermined. In the closed condition, the sample to be measured is positioned definedly, safely and stably in the collapsible cuvette which has two adapter parts 67, 68.

A further embodiment of the present invention represents magazining of the single-use items and is not shown in detail. From an easy to handle magazine, preferably in the form of a cartridge, the inserts 2, 3 for single-use can be inserted easily into the openings of a re-usable collapsible cuvette which are provided for this purpose. After use, the single-use inserts 2, 3 are pushed out of the collapsible adapter by hand or by way of a device or by way of a lug on the cartridge, and then thrown away. New inserts 2, 3 may then be inserted again.

The single-use items can also be combined with adapters that are realised as single-use items. Further possible is a combined single-use item with front and rear part from one tool, as the case may be also as a so-called two component injection moulded article.

Figure 26:
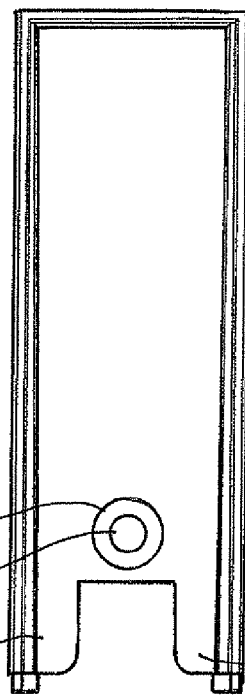
FIG. 26 cuvette with a capillary channel that is open towards two sides, in a side view.
Figure 27:
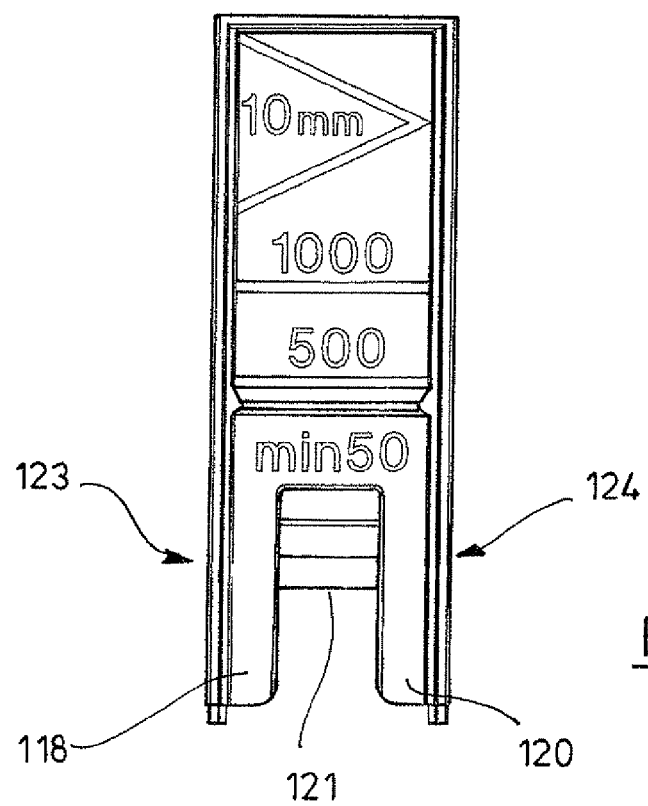
FIG. 27 the same cuvette in another side view.
Figure 28:
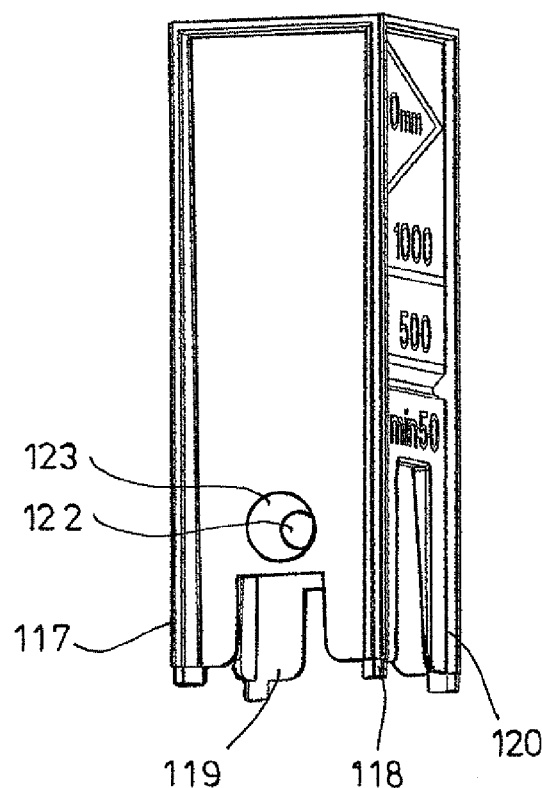
FIG. 28 the same cuvette, in a perspective view slantwise from two sides.

The cuvette of FIGS. 26 to 28 is not subject matter of this application. It is described only for the sake of illustration of the claimed invention.

The cuvette according to FIGS. 26 to 28 corresponds to a great extent to the cuvette according to the realisation example of DE 198 26 470 C1, which is incorporated by reference. However, in difference to the known cuvette, the box-like bottom part 121, arranged between the four feet 117, 118, 119, 120, is not opened at the inside towards a cavity of the cuvette, but is closed instead. Further, a channel 122, open towards both sides, runs through this bottom part 121, which has funnel-shaped expansions 123, 124 towards both outer sides.

The cuvette has the shape of a commercially available cuvette, so that it can be put into a conventional commercial photometer or spectrometer, respectively.

Crossing the channel 122 which is open on both sides, optical measurements can be performed. Through this, no light is guided through a plastics wall of the cuvette during the measurement, and thus, the measurement is not influenced. It is not necessary to measure a value for each empty cuvette.

The channel 122 tapers conically towards the outer sides of the cuvette, so that an overdosage results only in a marginal increase of the optical layer thickness. As a side effect, the cuvette receives a filling aid through this. A pipette point can be put on the expansions 123, 124 and the channel 122 be filled in this way, until the liquid reaches from the boarder between the conical and the cylindrical region of the channel 122. Now, the liquid completely fills the channel 122 and is held therein by adhesion or capillary action, respectively.

The conical expansions 123 can be made rough, on the one hand for achieving the stop effect, and on the other hand in order to avoid leaking of the liquid upon wrong handling. In addition to this, a trough can then be provided below the channel 122, which can receive the liquid that leaks out. As the channel 122 is significantly shorter than the overall width of the cuvette, the liquid can fall down only into this trough.

Figure 29:
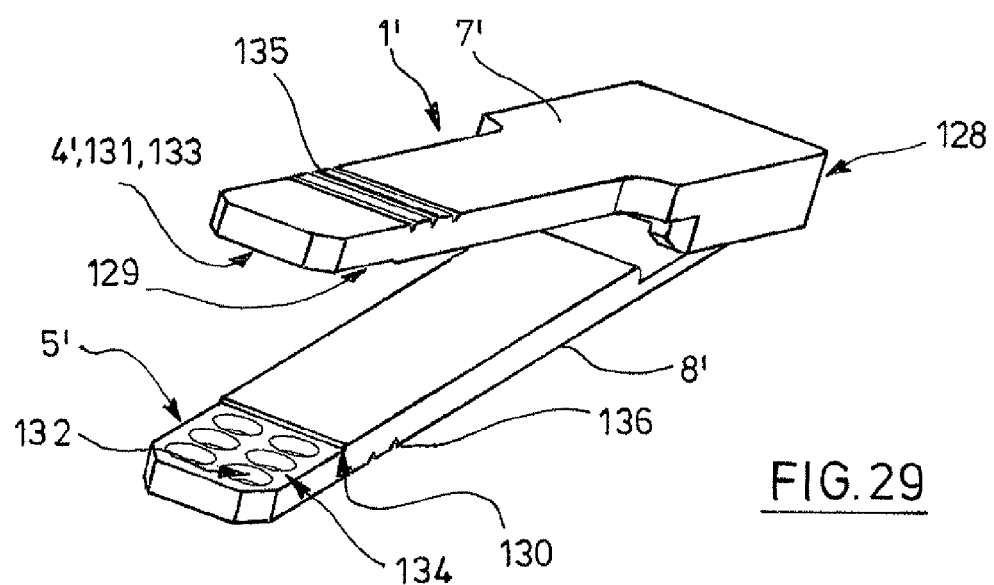
FIG. 29 an insert having plural measuring areas, the arms being swung apart, in a perspective view.
Figure 30:
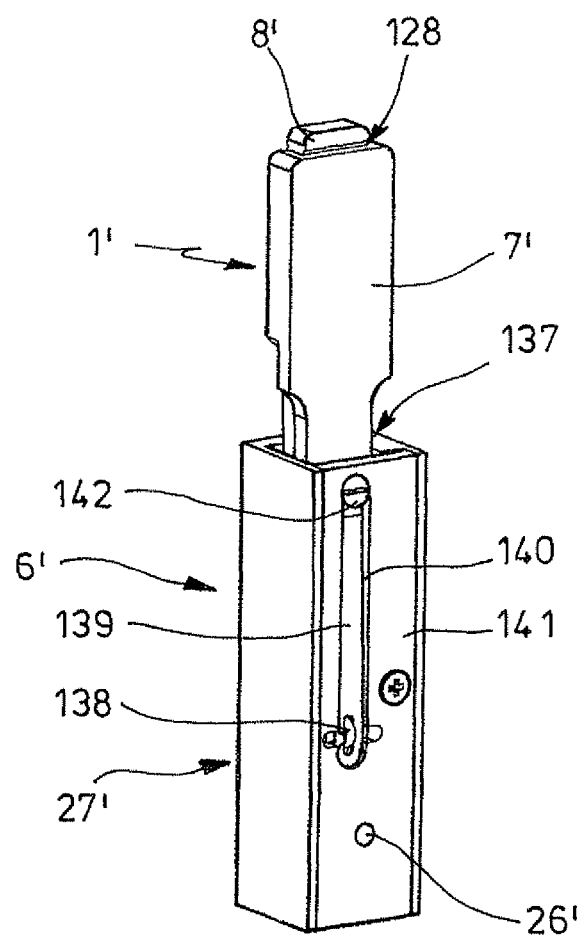
FIG. 30 the same insert, put into an adapter, in a perspective view.

In the realisation example of FIGS. 29 and 30, elements that correspond to elements of the realisation example of FIGS. 1 to 4 are provided with the same reference numerals, but in addition marked by a superscripted dash (').

The insert 1' is also realised in the kind of a pincette, wherein however, the arms 7', 8' are connected to each other on their upper ends by a film hinge 128.

Each strip-shaped arm 7', 8' has a shoulder 129, 130 or respectively a flattening at one end, in which the measuring areas 4', 5' are arranged. Each of these measuring areas 4', 5' has a group (6 in the example) of circular area portions 131, 132 for receiving sample liquid. One pair at a time of the area portions 131, 132 faces each other, so that it overlaps when the arms 7', 8' are swung together.

The area portions 131, 132 can be delimited from the rest of the measuring areas 4', 5' in that they are arranged deeper in little deepenings.

According to another embodiment, the area portions 131, 132 are arranged in deepenings and the area portions and the further area portions 133, 134 of the measuring areas 4', 5' which surround them have a hydrophobic coating. According to another embodiment, in which the area portions 131, 132 are not arranged in deepenings, the area portions 131, 132 have a hydrophilic coating, so that the samples are held thereon. According to another embodiment, in which the area portions are not arranged in deepenings, the further area portions 133, 134 of the measuring areas 4', 5' that surround them and which should not receive sample, have a hydrophobic coating. According to another embodiment, in which the area portions are not arranged in deepenings, the area portions 131, 132 have a hydrophilic coating and the further area portions 133, 134 that surround them have a hydrophobic coating.

When the arms 7', 8' are swung together, samples put on the area portions 131, 132 of the measuring areas 4', 5' are spanned up between the same.

Further, the arms 7', 8' each have a group of parallel grooves 135, 136 at the outer sides, which extend crosswise to their longitudinal axis. The grooves 135, 136 are disposed near to the free ends of the arms 7', 8'. In the example, the grooves 135, 136 on the different arms 7', 8' are disposed at equal distances from the free ends of the arms 7', 8'. In another embodiment, which is not shown, the grooves 135, 136 on the different arms 7', 8' are disposed at different heights. In still another embodiment, which is not shown, only one of the arms 7', 8' has grooves 135 or 136, respectively.

The insert 1' is made in one piece of plastics. Due to the elasticity of the film hinge 128, it takes on the configuration of FIG. 29 automatically.

The adapter 6' has the cuboid outline of a standard cuvette. It is essentially cuboid. It has an accommodation 137 with rectangular cross section, into which the insert 1' can be put in from the topside when the arms 7', 8' are swung together. An elastically acting projection 148 of the adapter 6' engages into the accommodation 137, which engages into one of the grooves 135 or 136 of the inserted insert 1'. Through this, the insert 1' is caught in the accommodation 137 in a height position.

The elastic catching projection 138 is realised as a small wheel, which is rotatably mounted at the end of a spring tongue 139. The spring tongue 139 is disposed in a longitudinal slot 140 of a side wall 141 of the adapter 6; and fixed at the lower end by way of a screw 142. As a consequence, the spring tongue 139 can be deflected within the longitudinal slot 140. The spring tongue 139 is deflected when the catching projection 138, realised as a small wheel, rolls over the outer side of an arm 7', 8'. Finally, the catching projection 138 falls into one of the grooves 135, 136, and through this, the insert 1' is fixed in the adapter 6' at a certain height.

On opposing side walls 141, 142, the adapter 6' has passage openings 26', 27' for the beam path of an optical measuring device. The passage openings 26', 27' are arranged in the lower third of the side walls 141, 142, approximately on the centre axis of the same.

In the catching position shown in FIG. 30, the area portions 131, 132, which are situated in FIG. 29 at the right downside on the measuring areas 4', 5' on the arms 7', 8', are arranged exactly between the passage openings 26', 27'. When the adapter 6' with the insert 1' is put into a cuvette shaft in this catching position, a sample can be measured between these area portions 131, 132 of the measuring areas 4', 5'. In the next deeper catching position, that sample moves into the beam path which is situated between the middle area portions 131, 132 of the right row, and so forth.

By pulling out the insert 1' from the accommodation 137, turning it about 180° around its longitudinal axis and putting it into the accommodation 137 anew, the samples between the area portions 131, 132, which are situated on the measuring areas 4', 5' on the arms 7', 8' in the left row at the downside in FIG. 29, can be brought into the beam path.

In another embodiment, filling the insert 1' when the arms 7', 8' are swung together is favoured in that the arms 7', 8' have small openings or respectively guiding mechanisms for a pipette on the two lateral borders of the measuring areas 4', 5', which extend from the lateral borders to the area portions 131, 132. A pipette point can be put into the openings or respectively guiding mechanisms, so that samples can be applied to the area portions 131, 132 of the collapsed measuring areas 4', 5' by way of a pipette.

The described realisation examples serve for illustrating the invention. However, the present invention is not limited to the realisation examples.

This completes the description of the preferred and alternate embodiments of the invention. Those skilled in the art may recognize other equivalents to the specific embodiment described herein which equivalents are intended to be encompassed by the claims attached hereto.

What is claimed is:

1. Cuvette, comprising an insert (1) having at least one measuring area (4, 5, 83, 84) on each one of two arms (7, 8, 67, 68) that are pivotally connected to each other, such that from a swung-apart condition, they can be swung together into a measuring position in which the two measuring areas (4, 5, 83, 84) have a distance for positioning a sample between the measuring areas (4, 5, 83, 84), and an adapter for positioning the two arms (7, 8, 67, 68) in a measuring position in a cuvette shaft of an optical measuring device with a sample between the two measuring areas (4, 5, 83, 84) in a beam path of the optical measuring device that crosses the cuvette shaft, wherein the adapter has an internal cavity having two parallel guide rails for accepting the insert for positioning the two arms (7, 87, 67, 68) and has a shape that is adapted to the cuvette shaft.

2. Cuvette according to claim 1, wherein the adapter for positioning the two arms (7, 8, 67, 68) is disposed in the measuring position in the standard cuvette shaft.

3. Cuvette according to claim 1, wherein the adapter for positioning the two arms (7, 8, 67, 68) is disposed in the measuring position in different positions in a cuvette shaft.

4. Cuvette according to claim 3, wherein the adapter for positioning the two arms (7, 8, 67, 68) is disposed in the measuring position in different height positions or different horizontal positions in a cuvette shaft.

5. Cuvette according to claim 1, wherein the adapter has a cross section of the arms (7, 8, 67, 68) swung together in the measuring position which is adapted to the cuvette shaft.

6. Cuvette according to claim 1, wherein the two arms (7, 8, 67, 68) are pivotally linked to each other via an articulation (69).

7. Cuvette according to claim 6, wherein the articulation (69') is a floating articulation.

8. Cuvette according to claim 1, which has a limiter for preventing the swinging together of the arms in the measuring position, or which has a locking mechanism for detachably locking (85 to 88, 89 to 92) the two arms (67, 68) in the measuring position.

9. Cuvette according to claim 1, which has the two measuring areas (83, 84) on two insert parts (81, 82) and which has means for detachably or not detachably holding the two insert parts on the arms (67, 68).

10. Cuvette according to claim 1, wherein at least one arm (67') has a recess (125), extending from the outer side of the arm (67') up to the measuring area (83'), for inserting a pipette point (127) and putting a sample between the measuring areas (83', 84') in the measuring position.

11. Cuvette according to claim 1, wherein the insert (1) is a pincette having the two measuring areas (4, 5) on the free ends of the arms (7, 8).

12. Cuvette according to claim 1, wherein the arms (7, 8) of the insert (1) taper towards the free ends.

13. Cuvette according to claim 1, wherein the insert (1) has a limiter for preventing the swinging together of the arms in a measuring position in which the two measuring areas (4, 5) have a certain distance from each other, or a locking mechanism for detachably locking the two arms (7, 8) in the measuring position.

14. Cuvette according to claim 1, wherein the locking mechanism for detachably holding comprise an accommodation of the adapter (6) and a contour of the insert (1) whose geometries are matched such that the insert in insertable into the accommodation into at least one certain position.

15. Cuvette according to claim 14, wherein the adapter (6') and the insert (1') have catching regions (129, 130) for detachably holding the insert (1') in different positions in the accommodation (131) of the adapter (6').

16. Cuvette according to claim 14, wherein the accommodation (131) is disposed asymmetrically with respect to the outline of the adapter (6').

17. Cuvette according to claim 1, wherein the two measuring areas (83, 84) or insert parts (81, 82) are optically transparent.

18. Cuvette according to claim 1, wherein the two measuring areas (83, 84) or insert parts (81, 82) are platelet-shaped.

19. Cuvette according to claim 1, wherein at least one measuring area (83, 84) or at least one insert part (81, 82) are made of plastics or quartz glass or glass and/or at least one arm or the insert or the adapter are made of plastics or metal.

20. Cuvette according to claim 1, wherein at least one measuring area (83, 84) has a planar pedestal.

21. Cuvette according to claim 1, wherein at least one measuring area (83, 84) has a deepening.

22. Cuvette according to claim 1, wherein at least one measuring area (83, 84) is hydrophobic.

23. Cuvette according to claim 22, wherein at least one measuring area (83, 84) has a less hydrophobic or hydrophilic spot.

24. Cuvette according to claim 1, wherein at least one measuring area (83, 84) is hydrophilic.

25. Cuvette according to claim 1, wherein the measuring areas (83, 84) are planar.

26. Cuvette according to claim 1, wherein the measuring areas (83, 84) are disposed in parallel in the measuring position.

27. Cuvette according to claim 1, wherein the distance of the measuring areas (83, 84) from each other is about 1 mm in the measuring position.

28. Cuvette according to claim 1, wherein the distances between the two measuring areas (83, 84) are dimensioned such that the volumes of the samples are 0.2 to 5 micro-liters.

29. Cuvette according to claim 1, which has at least one stop for limiting a light beam through the measuring areas (83, 84).

30. Adapter for at least one insert, said insert (1) having at least one measuring area on each of two arms (7, 8) that are pivotally connected with each other, wherein the adapter has an internal cavity having two parallel guide rails for accepting the insert and is insertable into a cuvette shaft of an optical measuring device which has a locking mechanism for detachably holding the at least one insert (1), so that the arms (7, 8) are swung together in a measuring position in which the measuring areas are in a distance from each other, and for positioning a sample between the measuring areas in a beam path of the optical measuring device that crosses the cuvette shaft.

* * * * *